(12) United States Patent
Rutkove et al.

(10) Patent No.: US 10,973,431 B2
(45) Date of Patent: Apr. 13, 2021

(54) ELECTRICAL IMPEDANCE MYOGRAPHY

(71) Applicant: Beth Israel Deaconess Medical Center, Inc., Boston, MA (US)

(72) Inventors: Seward B. Rutkove, Brookline, MA (US); Benjamin Sanchez Terrones, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 516 days.

(21) Appl. No.: 15/117,929

(22) PCT Filed: Feb. 13, 2015

(86) PCT No.: PCT/US2015/015961
§ 371 (c)(1),
(2) Date: Aug. 10, 2016

(87) PCT Pub. No.: WO2015/123603
PCT Pub. Date: Aug. 20, 2015

(65) Prior Publication Data
US 2017/0007151 A1 Jan. 12, 2017

Related U.S. Application Data

(60) Provisional application No. 61/940,329, filed on Feb. 14, 2014.

(51) Int. Cl.
*A61B 5/053* (2021.01)
*A61B 5/00* (2006.01)
*A61B 5/0537* (2021.01)

(52) U.S. Cl.
CPC ............ *A61B 5/0537* (2013.01); *A61B 5/053* (2013.01); *A61B 5/4519* (2013.01); *A61B 5/6843* (2013.01)

(58) Field of Classification Search
CPC ..... A61B 5/0537; A61B 5/053; A61B 5/4519; A61B 5/6843
See application file for complete search history.

(56) References Cited

U.S. PATENT DOCUMENTS 5,092,343 A * 3/1992 Spitzer ................ A61B 5/0488
600/515
9,014,797 B2 4/2015 Shiffman et al.
(Continued)

OTHER PUBLICATIONS

Christopher D. Moyes and Christophe M. R. LeMoine, Control of muscle bioenergetic gene expression: implications for allometric scaling relationships of glycolytic and oxidative enzymes, Accepted Jan. 18, 2005, Published 2005, The Journal of Experimental Biology 208, 1601-1610 (Year: 2005).*

(Continued)

*Primary Examiner* — Sean P Dougherty
(74) *Attorney, Agent, or Firm* — Wolf, Greenfield & Sacks, P.C.

(57) ABSTRACT

Electrical impedance myography (EIM) can be used for assessment and diagnosis of muscular disorders. EIM includes applying an electrical signal to a region of tissue and measuring a resulting signal. A characteristic of the region of tissue is determined based on the measurement. Performing EIM at different frequencies and modeling one or more impedance metrics as a function of frequency may provide impedance model parameters that can aid in the assessment and diagnosis. Devices are described that facilitate assessment and diagnosis using EIM.

18 Claims, 30 Drawing Sheets

(56) References Cited

U.S. PATENT DOCUMENTS

| | | | |
|---|---|---|---|
| 9,061,128 B2* | 6/2015 | Hall | A61P 35/00 |
| 9,962,096 B1* | 5/2018 | Kosierkiewicz | A61B 5/04012 |
| 9,974,463 B2 | 5/2018 | Rutkove et al. | |
| 10,357,513 B2* | 7/2019 | Braithwaite | A61K 9/0026 |
| 2003/0105411 A1 | 6/2003 | Smallwood et al. | |
| 2004/0082877 A1* | 4/2004 | Kouou | A61B 5/0537 |
| | | | 600/546 |
| 2004/0254617 A1* | 12/2004 | Hemmerling | A61B 7/006 |
| | | | 607/48 |
| 2006/0247543 A1 | 11/2006 | Cornish et al. | |
| 2007/0027402 A1* | 2/2007 | Levin | A61B 5/4872 |
| | | | 600/547 |
| 2010/0268109 A1 | 10/2010 | Wang | |
| 2010/0292603 A1 | 11/2010 | Shiffman et al. | |
| 2011/0054344 A1* | 3/2011 | Slizynski | A61B 5/053 |
| | | | 600/547 |
| 2011/0196262 A1 | 8/2011 | McLeod et al. | |
| 2011/0208084 A1* | 8/2011 | Seoane Martinez | A61B 5/053 |
| | | | 600/547 |
| 2011/0312751 A1 | 12/2011 | Azim et al. | |
| 2012/0245436 A1* | 9/2012 | Rutkove | A61B 5/053 |
| | | | 600/301 |
| 2012/0323136 A1 | 12/2012 | Shiffman et al. | |
| 2013/0197340 A1* | 8/2013 | Sanders | A61B 5/02007 |
| | | | 600/384 |
| 2013/0268240 A1* | 10/2013 | Thorn | A61B 5/1118 |
| | | | 702/180 |
| 2015/0196220 A1 | 7/2015 | Rutkove et al. | |
| 2018/0235494 A1* | 8/2018 | Kosierkiewicz | A61B 5/04012 |
| 2019/0069801 A1 | 3/2019 | Rutkove et al. | |
| 2020/0297235 A1 | 9/2020 | Sanchez et al. | |

OTHER PUBLICATIONS

International Search Report, dated Jun. 24, 2015, from corresponding International Application No. PCT/US2015/015961.
Invitation to Pay Additional Fees for Application No. PCT/US2015/015961 dated May 13, 2015.
International Search Report and Written Opinion for Application No. PCT/US2015/015961 dated Jul. 14, 2015.
International Preliminary Report on Patentability for Application No. PCT/US2015/015961 dated Aug. 25, 2016.

* cited by examiner

ELECTRICAL IMPEDANCE MYOGRAPHY

CROSS-REFERENCE TO RELATED APPLICATIONS

This application is the national phase of International Application No. PCT/US2015/015961, filed on Feb. 13, 2015, which claims the priority benefit of U.S. Provisional Application No. 61/940,329, filed Feb. 14, 2014, both of which applications are hereby incorporated by reference to the maximum extent allowable by law.

FEDERALLY SPONSORED RESEARCH

This invention was made with government support under grants R01NS055099 and R01AR060850 awarded by the National Institutes of Health. The Government has certain rights in the invention.

BACKGROUND OF INVENTION

Neuromuscular diseases encompass a large collection of disorders, ranging from relatively mild conditions such as focal compression neuropathies and nerve root injuries, to severe and life-threatening syndromes, including amyotrophic lateral sclerosis (ALS) and muscular dystrophies. These disorders may lead to muscle atrophy and weakness, caused either by injury to or disease of the neuron (neurogenic disorders), the neuromuscular junction, or the muscle cell itself (myopathic disorders). Another disorder, disuse atrophy, may occur when a limb is immobilized or a patient is bed-bound for a prolonged period of time, although not classically considered a neuromuscular disorder, also produces substantial morbidity.

Neuromuscular diseases have been assessed and diagnosed using various techniques, including nerve condition studies, needle electromyography, muscle imaging, muscle biopsy and genetic testing. However, the initial assessment of the neuromuscular diseases has advanced relatively little beyond conventional needle electromyography and nerve conduction techniques. Similarly, there have been few good approaches to the assessment of disuse atrophy and dysfunction.

Nerve conduction studies (NCSs) and needle electromyography (EMG) are often the first tests obtained when evaluating a patient for neuromuscular causes of atrophy. NCSs involve stimulation of a nerve with one set of electrodes and recording the resulting muscle or nerve potential with a second set of electrodes. Although useful for evaluating nerve pathology, NCSs are of limited use for evaluating muscle disease or disuse states. The stimuli can be uncomfortable and only a relatively limited set of distal muscles in the arms and legs can be evaluated.

Needle electromyography is geared more specifically to muscle evaluation. Needle electromyography can provide a quick survey of muscles to determine whether they are being affected by neurogenic injury or myopathic injury. However, the test has considerable limitations. First, needle electromyography is very subjective because physicians qualitatively assess the attributes of motor unit action potentials (MUAPs) as they rapidly pass across an oscilloscopic display. Second, there are substantial limitations with respect to the sensitivity of needle electromyography. It is a common experience amongst electromyographers that only with extensive probing are one or two questionably abnormal MUAPs identified. Third, the lack of quantifiable results makes EMG an unsuitable modality for following disease progression/remission. Finally, needle EMG remains a somewhat painful, invasive procedure and can thus only be used in a very limited fashion in children.

Imaging techniques such as magnetic resonance imaging (MRI) and ultrasound have found some use in muscle atrophy assessment. For example, MRI can be used to identify muscles with active inflammation to assist with biopsy site choice in patients with myositis. However, MRI has otherwise remained of limited use since it is difficult to evaluate different areas of the body, is costly, cannot easily assess dynamic muscle states during muscle contraction, and may not be used in patients with pacemakers and implanted defibrillators. Ultrasound has found limited use in neuromuscular disease and disuse atrophy assessment, and remains very qualitative.

Muscle biopsy is another test for evaluation of muscle disease and can be helpful in arriving at a specific diagnosis. Muscle biopsy frequently yields limited or contradictory information and may be unsuitable for monitoring progression of atrophy because of its inherent invasiveness. Given that many diseases are patchy (i.e., regions of diseased muscle tissue is interspersed throughout ostensibly healthy muscle tissue), a negative biopsy does not exclude disease, and repeat biopsies sometimes need to be performed.

Genetic tests can be very useful for assisting in the evaluation of a number of mostly rare conditions (such as the muscular dystrophies), but is expensive and not relevant to a variety of the most common, acquired conditions.

SUMMARY

According to an embodiment, there is provided a method and apparatus for applying a plurality of electrical signals having a plurality of frequencies to a region of tissue, wherein an electrical signal of the plurality of electrical signals has one frequency of the plurality of frequencies; obtaining a plurality of measurements from the region of tissue in response to applying the plurality of electrical signals, wherein each measurement of the plurality of measurements is indicative of an electrical parameter of the region of tissue at one frequency of the plurality of frequencies; determining at least one impedance model parameter associated with an impedance model, at least in part, by fitting a plurality of values for the electrical parameter over the plurality of frequencies to the impedance model; and identifying at least one biological characteristic of the region of tissue based on the at least one impedance model parameter.

According to an embodiment, the at least one biological characteristic is a cell type. According to an embodiment, the cell type is at least one of fast-twitch and slow-twitch. According to an embodiment, the at least one biological characteristic is an amount of an intracellular component. According to an embodiment, the at least one biological characteristic is a structural feature of an intracellular component. According to an embodiment, the intracellular component is mitochondrion. According to an embodiment, the method further comprises assessing a muscle condition based on the at least one biological characteristic. According to an embodiment, further comprises diagnosing a disease state based on the at least one biological characteristic.

According to an embodiment, the impedance model is a Cole-Cole impedance model and the at least one impedance model parameter is at least one of resistance at direct current (DC), $R_0$, resistance as $\omega \to \infty$, $R_\infty$, central frequency, $f_c$, and dimensionless parameter, $\alpha$. According to an embodiment, the resistance at direct current and resistance as $\omega \to \infty$ indicate a characteristic of the volume of the cells in the biological tissue. According to an embodiment, the dimensionless parameter, α, indicates a degree of uniformity of fiber size when the biological material includes muscle fibers.

According to an embodiment, the center frequency indicates a diameter of muscle fiber when the biological tissue includes a muscle fiber. According to an embodiment, the center frequency is monitored before, during, and after a muscle contraction and indicates a condition of a muscle located at the region of tissue. According to an embodiment, the at least one impedance model parameter is monitored before and after a muscle contraction and determines a change of the region of tissue from the contraction.

According to an embodiment, there is provided a method and apparatus for identifying characteristics of biological tissue, comprising: positioning a pair of first electrodes along a first axis on the biological tissue; positioning a pair of second electrodes on the biological tissue along the first axis and between the first electrodes; controlling an alternating current in the first electrodes; varying the frequency of the alternating current over at least one frequency value; measuring at least one voltage from the pair of second electrodes; determining at least one material property value based on the alternating current over the at least one frequency value and the at least one voltage; and identifying at least one substructure characteristic of the biological tissue based on the at least one material property value.

According to an embodiment, the biological material includes muscle. According to an embodiment, the first axis aligns parallel to muscle fibers in the muscle. According to an embodiment, the first axis aligns perpendicular to muscle fibers in the muscle. According to an embodiment, the alternating current is sinusoidal. According to an embodiment, the at least one frequency value ranges from 1 kHz to 10 MHz.

According to an embodiment, determining the at least one material property value comprises: determining, for each frequency, a resistance and a reactance of the biological material based on the alternating current over the at least one frequency value and the at least one voltage; determining a conductivity and a relative permittivity for the biological material based on the resistance and the reactance; determining a complex resistivity based on the conductivity and the relative permittivity; and determining a plurality of material property values based on fitting the complex resistivity with a mathematical expression.

According to an embodiment, the mathematical expression is a Cole-Cole expression and the at least one material property value includes a resistivity at direct current (DC), $\rho 0$, a resistivity as $\omega \to \infty$, $\rho\infty$, a central frequency, fc, and a dimensionless parameter, α. According to an embodiment, the at least one substructure characteristic is a cell type. According to an embodiment, the at least one substructure characteristic is a distribution of an intracellular component. According to an embodiment, the at least one substructure characteristic is a structural feature of an intracellular component. According to an embodiment, the intracellular component is mitochondrion. According to an embodiment, a disease state can be distinguished based on the at least one substructure characteristic. According to an embodiment, the at least one substructure characteristic is measured over time to evaluate the efficacy of a drug in changing the biological tissue.

According to an embodiment, the at least one substructure characteristic is a relative proportion of a plurality of cell types. According to an embodiment, the plurality of cell types are a fast-twitch and a slow-twitch. According to an embodiment, the biological tissue is part of an organism and the pair of first electrodes and the pair of second electrodes contact a surface of the organism.

According to an embodiment, there is provided a method and apparatus for performing an impedance measurement for biological tissue having at least two cell types, comprising: positioning a first pair of electrodes on the biological tissue along a first axis; positioning a second pair of electrodes on the biological tissue along the first axis and between the first pair of electrodes; controlling an alternating current in the first pair of electrodes; varying the frequency of the alternating current over a plurality of frequency values; measuring at least one voltage from the second pair of electrodes; determining a plurality of impedance measurements based on the alternating current over a plurality of frequency values and the at least one voltage; and calculating a ratio of the plurality of impedance measurements.

According to an embodiment, the plurality of frequency values include a first frequency and a second frequency, the first frequency produces a first impedance measurement optimized for a first cell type, the second frequency produces a second impedance measurement optimized for a second cell type. According to an embodiment, the first cell type is muscle and the second cell type is fat. According to an embodiment, the first frequency is 50 kHz and the second frequency is 200 kHz. According to an embodiment, the plurality of impedance measurements are phase values. According to an embodiment, the plurality of frequency values are 50 kHz and 200 kHz.

According to an embodiment, there is provided a method and apparatus for measuring impedance of biological tissue in an organism, comprising: contacting an electrode array to the biological tissue, the electrode array having a plurality of electrodes; controlling an AC input signal to the electrode array; measuring an output signal from the electrode array; determining at least one impedance measurement based on the input signal and output signal; determining a status of the biological tissue based on the at least one impedance measurement; and determining a status of the organism based on the at least one impedance measurement.

According to an embodiment, the biological tissue is a tongue of an organism. According to an embodiment, the status of the biological tissue is a condition of a tongue. According to an embodiment, the biological tissue is facial muscle of an organism. According to an embodiment, the at least one impedance measurement is a phase value. According to an embodiment, the status of the organism is a measure of disease severity. According to an embodiment, the measure of disease severity is bulbar dysfunction when the organism has amyotrophic lateral sclerosis (ALS).

According to an embodiment, there is provided a method and apparatus for measuring impedance in biological tissue of an organism before, during and after a tissue contraction, comprising: positioning an electrode array on the biological tissue, the electrode array including electrodes along a first axis and an inner pair of electrodes between an outer pair electrodes; controlling an AC input signal to the outer pair of electrodes; measuring an output signal from the inner pair of electrodes; varying the frequency of the AC input signal over at least one frequency value; modeling the input signal and the output signal with a mathematical expression; determining at least one impedance parameter based on a fit of the mathematical expression to the input signal and the output signal; and tracking the at least one impedance parameter before, during, and after the tissue contraction.

According to an embodiment, the mathematical expression is a Cole-Cole expression and the plurality of impedance parameters include resistance at direct current (DC), R0, resistance as $\omega \to \infty$, R∞, central frequency, fc, and dimensionless parameter, $\alpha$. According to an embodiment, resistance at direct current and resistance as $\omega \to \infty$ indicate a characteristic of the volume of the cells in the biological tissue. According to an embodiment, a dimensionless parameter, $\alpha$, indicates a degree of uniformity of fiber size when the biological material includes muscle fibers. According to an embodiment, the center frequency indicates a diameter of muscle fiber when the biological tissue includes a muscle fiber. According to an embodiment, the center frequency tracked before, during, and after the contraction provides an indicator of the disease state of the organism.

According to an embodiment, the indicator of the disease state is measured over time to determine a response from therapy. According to an embodiment, the at least one impedance parameter before and after the contraction determine an alteration of the biological tissue from the contraction. According to an embodiment, the at least one impedance parameter before, during, and after the contraction determine a status of health of the biological tissue.

According to an embodiment, there is provided a method and apparatus for determining the size of muscle fibers in biological tissue of an organism, comprising: positioning an electrode array to contact the biological tissue, the electrode array including electrodes along a first axis, an inner pair of electrodes between an outer pair electrodes; controlling an AC input signal to the outer pair of electrodes; measuring an output signal from the inner pair of electrodes; varying the frequency of the AC input signal over at least one frequency value; determining at least one impedance value based on the input signal and output signal; identifying a peak frequency based on the at least one impedance value; and determining a muscle fiber size based on the peak frequency.

According to an embodiment, the muscle fiber size is the cross-sectional diameter. According to an embodiment, the muscle fiber size approximates the average size for a plurality of muscle fibers in the biological tissue. According to an embodiment, the at least one impedance value is reactance. According to an embodiment, the at least one impedance value is phase. According to an embodiment, determining a muscle fiber size based on the peak frequency includes matching the peak frequency to a look-up table. According to an embodiment, the look-up table is created by determining a plurality of peak frequency values for a plurality of muscle fibers with known size values. According to an embodiment, the peak frequency is a measure of health of the organism. According to an embodiment, the peak frequency is an indicator of disease status in the organism.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
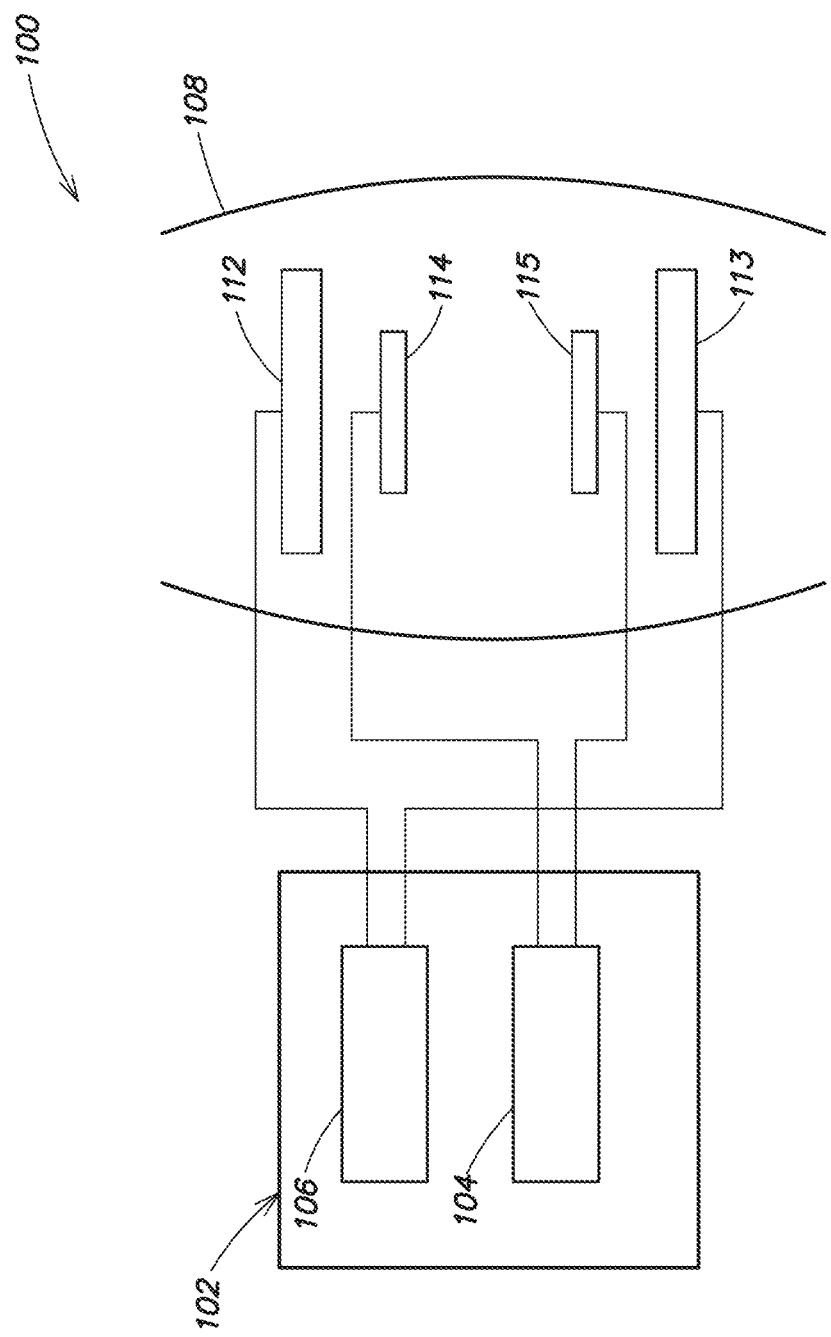
FIG. 1 is a diagram illustrating an example of a device that performs electrical impedance myography, according to one embodiment.

Embodiments relate to methods and devices for electrical impedance myography (EIM). Muscle condition can be assessed and diagnosed based on the measured electrical signals obtained by an EIM device. Analysis of the electrical signals can identify characteristics of a muscle region including cellular and intracellular features such as muscle fiber size, muscle type, an amount of mitochondria, and glycogen content. In some embodiments, the quantitative nature of the techniques described herein can facilitate the identification of the progression of a neuromuscular disorder and the evaluation of efforts to prevent further progression of the neuromuscular disorder. For example, the effectiveness of treatments for neuromuscular disorders may be evaluated using the techniques described herein. Additionally, the techniques described herein can be used to evaluate muscle fitness, condition, and effect of exercise in individuals.

To perform an EIM technique, an electrical signal (e.g. electrical current) may be applied to the region of tissue using electrodes applied to the skin. Various characteristics can be determined based on the electrical parameters that are measured for the region, such as the impedance, reactance, resistance, and/or phase shift. In contrast to existing techniques for assessing and diagnosing neuromuscular disease, EIM may be more rapid, more quantitative, less invasive and more repeatable. EIM can be used for the assessment of muscle conditions, and more specifically, neuromuscular disease. However, it should be appreciated that EIM is not limited to the assessment of neuromuscular disease, as any other suitable tissue characteristic(s) may be measured using EIM, such as the amount of muscle atrophy that has occurred through disuse of a muscle (or more rarely, hypertrophy), as the aspects are not limited in this respect. Additionally or alternatively, EIM can be used to assess fitness of muscle with training and with injury after overuse or due to trauma.

Some embodiments relate to methods and devices for multi-frequency EIM, which involves performing measurements at least two different frequencies of electrical signals. Because the electrical parameters of a muscle can be dependent on the frequency of an alternating current applied to a muscle, measurements of the muscle impedance for a plurality of frequencies can be utilized to facilitate diagnosis of muscle condition, and to differentiate between normal and abnormal muscle tissue. In some embodiments, multi-frequency measurements may reduce the impact of subcutaneous fat on the muscle health measurements by taking a ratio or difference of measurements at two frequencies in order to provide a more accurate measure of muscle status. In some embodiments, impedance measurements performed over several frequencies may be fit to an impedance model in order to assist in identifying intra-cellular and cellular characteristics such as muscle fiber size, muscle type (e.g., type 1, type 2), and number of mitochondria. By identifying such intra-cellular and cellular characteristics, an assessment and prediction of exercise skill sets (e.g., long-distance, sprinting) well-suited for the muscle may be determined.

Multi-frequency EIM can be performed by varying the frequency of the alternating current applied to the muscle of group of muscles. For example the frequency that is applied may be in the range between about 1 kHz and about 20 MHz, but embodiments are not limited to this particular frequency range, as any other suitable frequency range can be used. The alternating current can be injected via one set of surface electrodes (referred to as current-injecting electrodes), and the resulting voltage patterns can be recorded via a second set of surface electrodes (referred to as voltage-recording electrodes). Based on the measurement of the injected current's magnitude, an impedance instrument can convert the voltage signals into a resistance (R) and reactance (X), for each applied frequency. From these parameters, a phase (A) may be computed, for each applied frequency. However, any suitable electrical parameters may be measured and/or calculated for evaluation of muscle tissue, as the invention is not limited in this respect.

The current-injecting and voltage-recording electrodes may form an array of electrodes adopting a configuration such that the electrode array operates as a single composite electrode. In some embodiments, an array of electrodes may be arranged linearly, with an outer pair of electrodes configured as current-injecting electrodes and an inner pair of electrodes configured as voltage-recording electrodes. In some embodiments, an array of electrodes may be arranged in a multiple concentric square configuration with electrodes positioned at the sides of the squares. In some embodiments, an array of electrodes may be arranged in a multiple concentric ring configuration with sets of electrodes arranged into a ring. Any suitable number of rings, as well as other geometric configurations, may be used in the electrode array as embodiments are not limited in this respect.

In some embodiments, changes in muscle condition (e.g., a progression of a disease, improvement with training) along a certain direction in the muscle tissue may be detected using different sets of current-injecting and voltage-recording electrodes. As such, impedance measurements obtained using one set of electrodes may be compared to impedance measurements obtained using another set of electrodes. Other suitable combinations of the sets of electrodes may be utilized.

In some embodiments, in the electrode array of an EIM probe, functions of the current-injecting and voltage-recording electrodes may be interchangeable. In other words, each of the individual electrodes or a group of electrodes may be programmed to operate as either excitation or pickup electrodes.

Some embodiments relate to a method and apparatus for performing multi directional (also referred to as rotational EIM). Because the measured electrical parameters of a muscle can be anisotropic, and therefore dependent on the orientation of the measurement electrodes relative to the muscle fibers, electrical parameter measurements in a plurality of different directions can be utilized to facilitate diagnosis of muscle condition, and to differentiate between normal and abnormal muscle tissue. In some embodiments, a method and apparatus is provided for both multi-frequency and multi-directional EIM. Such combined measurements can provide more diagnostic information than multi-frequency or multi-directional EIM alone.

In some embodiments, a method and apparatus is provided for performing EIM during contraction of a muscle, and may be referred to as dynamic EIM. The contraction can be voluntary or electrically induced. In some embodiments, the EIM probe may be used to obtain impedance measurements during alternating contraction and relaxation of the underlying muscle or muscle group(s). In such scenarios, any suitable combination of contraction and relaxation of the muscles may be employed. Changes in impedance measurements with contraction of the muscles may provide useful data that may be indicative of neuromuscular abnormalities of the muscles. Such data may thus be used to differentiate between normal and diseased tissues and to identify a type of a disease and/or a stage of a disease. In some embodiments, the EIM probe may be supplemented with a suitable device (e.g., a force transducer) to measure the muscle contraction. Hence, simultaneous measurements of impedance and contraction force of the muscle may be obtained. In some embodiments, during obtaining such simultaneous measurements, electrical nerve stimulation may be implemented to assess various properties of the muscle.

In yet other embodiments, a combination of multi-frequency, multi-directional, and/or dynamic EIM measurements can also be used to assess muscle condition, effects of training, detraining, and injury. In some embodiments, a combination of multi-frequency, multi-directional, and/or dynamic EIM measurements can also be used to differentiate between different types of abnormal muscle conditions, including neuromuscular conditions (e.g., amyotrophic lateral sclerosis (ALS), inflammatory myopathy, bulbar dysfunction) and neurogenic conditions. A stage of a disease may be assessed as well. It should be appreciated that any of the aforementioned embodiments can be performed on one or more muscles including quadriceps, biceps, tibialis anterior, etc., as embodiments are not limited to any specific muscle or muscle group.

In some embodiments, a method and apparatus are provided for use of a composite signal comprising multiple tones that makes possible measurements of impedance of muscle tissue at multiple frequencies simultaneously. This may reduce a time required to obtain the measurements.

As part of assessing and diagnosing a muscle condition, analysis of multi-frequency impedance measurements may include comparison to an impedance model. In some embodiments, one or more electrical properties as a function of frequency may be fitted to an impedance model (e.g., Cole-Cole impedance model), and values for one or more model parameters of the impedance model may be identified. Based on assessment of the model parameters with known muscle characteristics, values for the model parameters may indicate certain cellular and/or intra-cellular characteristics of the measured muscle such as muscle fiber size, muscle type, number of mitochondria, and/or t-tubule system. By obtaining information specific to the cellular and sub-cellular of muscle, assessment and diagnosis may focus on conditions affecting those structural components of the cell. In this manner, the electrical signals obtained by EIM measurements can correlate as detecting intra-cellular and/or cellular components, providing a non-invasive measure of a muscle's condition.

In some embodiments, the range of frequencies over which EIM measurements are performed may be selected in order to identify particular cellular components. Identification of intracellular components may include performing EIM measurements at frequencies above 1 MHz in order to effectively penetrate the cell membrane.

In some embodiments, a relationship between an impedance parameter and a characteristic of the muscle may be identified, and assessment of a measured muscle may include comparing a value of the impedance parameter based on measurements to the relationship in order to identify the muscle characteristic. For example, a center or peak frequency may identify a muscle fiber size indicating an average size of the fibers that make up the muscle in the region of tissue being measured. A specific peak value may correspond to a particular fiber size which can be used to evaluate the condition of the muscle such as when assessing the effects of training or therapy on muscle fiber size. In some embodiments, impedance measurements may be performed during a muscle contraction and, by identifying aspects of the structural components of the muscle cells, any changes the muscle undergoes during contraction can be assessed.

In some embodiments, the EIM measurement system may allow, in addition to obtaining impedance measurements, to obtain measurements of different additional parameters to thus improve efficiency of the system and increase accuracy of assessment and/or diagnosis of a muscle condition. These additional measurements may be collected as part of monitoring of different factors that may affect the quality of the impedance measurements. Accordingly, the EIM system may comprise one or more suitable devices (e.g., suitable sensors) to obtain the measurements of the additional parameters. The devices may be associated with an EIM probe in any suitable manner. For example, one or more devices may be incorporated in a suitable location at a head of the EIM probe.

The additional parameters may provide information on the patient's skin condition, quality of EIM measurements being obtained and other factors. Thus, the additional devices may be used to obtain measurements of such parameters as, for example, a temperature of the skin in the region to which the EIM probe is applied, the moisture content of the skin in this region, and pressure with which the EIM probe is applied. Furthermore, measurements of electrode contact quality reflecting how closely the electrodes of the electrode array of the EIM probe contact the skin of the region being analyzed may be obtained. However, it should be appreciated that any other suitable parameters may be obtained in addition to impedance measurements obtained using the EIM probe.

In some embodiments, the EIM measurement system may comprise one or more suitable sensors to measure a temperature of the skin to which the EIM probe is applied. Variations in the skin and tissue (e.g., muscle) temperature may affect impedance measurements. Accordingly, temperature of the limbs or other parts of the patient's body can be adjusted to a specific temperature (e.g., 34° C.), which may be inconvenient and cumbersome. Accordingly, including a temperature sensor, such as a thermocouple or other suitable device, within the EIM probe may allow performing measurement of the skin temperature simultaneously with the impedance measurements. One or more of the suitable temperature sensors may be placed in any suitable location in proximity to the electrode array of the EIM probe. Thus, in some embodiments, the temperature sensor may be placed in the center of the electrode array. Though, it should be appreciated that embodiments are not limited in this respect and a temperature sensor may be placed in any suitable location within or near the electrode array.

In embodiments where measurements of a temperature of the skin are obtained along with impedance measurements, the impedance measurements may be adjusted in accordance with variations in the temperature of the skin that may occur during taking EIM measurements. In some scenarios, an automatic adjustment (or correction) for the variations in the temperature may be performed so that EIM measurements are presented to a user as adjusted, or corrected, values for the variations in the temperature of the skin of the patient. Such adjustment may result in an improved accuracy of the impedance measurements. Also, this may improve an accuracy and reliability of comparison of impedance measurements obtained from a region of a patient's body at different periods of time.

Furthermore, in some embodiments, the EIM measurement system may be used to obtain electrode contact quality measurements indicative of how closely the electrodes of the electrode array of the EIM probe contact the skin of the region where the EIM probe is applied.

In some situations, one or more electrodes of the electrode array may not contact the surface of the patient's skin where the EIM probe is applied sufficiently well to obtain impedance measurements with good resolution. For example, the EIM probe may be applied such that the electrodes are positioned at a distance from the surface of the skin that is larger than a predetermined distance at which impedance measurements with good resolution may be obtained. This may occur due to various conditions related to characteristics of the patient's skin. For example, the skin may be dry, callused, injured or abnormal in any other manner that compromises effective electrical transmission and measurement via the electrode array. Other factors may affect quality of the electrode contact as well. For example, when the EIM probe is applied to a surface of a patient's limb, a head of the probe bearing the electrode array may not contact the surface of the skin evenly so that one or more of the electrodes of the electrode array may not be in contact with the surface of the limb curve. In some circumstances, reliable impedance measurements may not be obtained at all.

To account for the above conditions, the EIM measurement system may measure electrode contact quality reflecting how closely each of the electrodes of the electrode array of the EIM probe contacts the skin of the region being analyzed. The electrode contact quality may be measured as a degree of contact between an electrode and a surface of the region being analyzed. The degree of contact may then be compared to a predetermined threshold. Any suitable components and techniques may be used to measure the electrode contact quality. For example, suitable characteristics of the skin in a region to which the EIM probe is applied may be measured. Thus, in some embodiments, the electrode contact quality measurements may include measuring the moisture content of the skin. Any suitable device, such as a hydrometer, may be used to measure the moisture content of the skin.

Other characteristics of the skin may be measured as well. Also, the impedance measurements obtained using the electrode array may be used to determine the electrode contact quality. Quality and accuracy of impedance measurements obtained using an EIM measurement system may depend on a force with which an EIM probe is being applied to a region of tissue. Thus, in some embodiments, the EIM measurement system may, in addition to obtaining impedance measurements, monitor force with which the EIM probe is being applied to a region of tissue. The force may be monitored using any suitable device. For example, one or more pressure sensors may be employed. The pressure sensor may be embedded into or otherwise associated with the EIM measurement system in any suitable manner (e.g., located within the EIM probe) and may be any suitable device.

During the EIM measurements, it may be useful to apply the EIM probe to a region of tissue with uniform force to ensure reproducibility of the results and to facilitate their assessment. The results of the EIM measurements may be easier to compare between different group(s) of muscles of the same patient and/or different patients. Furthermore, the pressure sensor may provide, during a time when the EIM probe is applied to the patient's body, an indication to a user of the EIM probe of a value of the force being applied, including an indication of whether an inadequate, adequate, or excessive force is being applied. Furthermore, more than one pressure sensors may be used to ensure that the pressure is being applied equally to entire surface of the electrode array. The impedance measurements may be adjusted for variations in force with which the EIM probe is applied to a region of tissue of the patient.

As discussed above, electrodes in an electrode array of the EIM probe may form different patterns, a non-limiting example of which includes multiple concentric rings. The electrode array may also be of different sizes so that smaller arrays may be used for assessment of conditions of smaller muscles or muscles of children. In some embodiments, an electrode array may have a size suitable for assessing a particular region of a body. For example, an electrode array may be sized for positioning within a person's mouth to assess the conditions of the muscle of the person's tongue. In the electrode array, the electrodes may be fixedly attached to a base such as a printed circuit board or other suitable base. The base may be rotatable. Though, the electrode array may be designed to be disposable, meaning that the electrode array may be attached to the body of the EIM probe so that the array may be easily removed. Such electrode array may be referred to a disposable electrode array. Thus, the EIM probe may be used with different electrode arrays. Also, the disposable electrode array may be manufactured to be sterile, which may help lower a risk of spreading infections (e.g., bacterial infections such as those caused by *Staphylococcus aureus*) between patients.

When the EIM probe is adapted to bear a disposable electrode array, the probe may be equipped with a mechanism for easy attachment and removal of the array from the probe (e.g., a head of the probe). In some embodiments, the baking of the electrode array may be made of a firm plastic and the electrodes may be made from different other materials. The electrode array may be then clipped onto the EIM probe via a suitable locking mechanism and then disposed of via a suitable release mechanism when EIM measurements are completed.

FIG. 1 illustrates an example of an apparatus 100 that may be used to perform multi-frequency EIM, according to one embodiment. Apparatus 100 includes electrodes 112-115, and also circuit 102 that measures and generates electrical signals using signal measurement circuit 104 and signal generation circuit 106. Apparatus 100 may include any components in any arrangement capable of delivering electrical signals and measuring electrical signals resulting from the electrical signals delivered, as the aspects are not limited in this respect.

In this embodiment, signal generating circuit 106 is coupled to two spaced-apart current-injecting electrodes 112 and 113, which may be applied to region of tissue 108. Using electrodes 112 and 113, an electrical signal is applied to region of tissue 108, for example, by passing an electrical current through the skin and into the region of tissue. The electrical signal that is applied may be any suitable signal, such as a predetermined voltage potential or a predetermined current. The electrodes may be isolated from a supply voltage using a transformer or any suitable device, such that a "floating" signal, and applied to the patient, thus enhancing the safety of the procedure.

In one example, the signal that is applied to current-injecting electrodes 112 and 113 may be a sinusoidally varying voltage having a magnitude of approximately 1 volt (peak-to-peak) and a frequency between approximately 1 kilohertz and approximately 20 megahertz. As a consequence of applying this signal, electric current is injected into region of tissue 108. However, it should be appreciated that these values of voltage, shape, and frequency are provided merely by way of illustration, as embodiments are not limited in these respects. Furthermore, any suitable circuit and/or technique may be used to generate the electrical signal applied to the region of tissue, as embodiments are not limited for use with any particular method of electrical signal generation and/or application.

Signal measuring circuit 104 is coupled to two spaced-apart voltage-measuring electrodes 114 and 115. While the generated signal is applied to tissue region 108 by signal generation circuit 106, signal measurement circuit 104 measures a signal at the tissue region using voltage-measuring electrodes 114 and 115. The signal that is measured may be a voltage difference between the two electrodes that results from the generated signal. Any suitable circuit and/or technique may be used to measure the signal, as embodiments are not limited in this respect.

Circuit 102 may analyze the measured signal and determine a characteristic of the region of tissue based on the measured signal. Any suitable property of the signal may be measured, such as the magnitude, phase, impedance, resistance, and reactance or any suitable combination thereof. In some embodiments, the measured voltage difference at electrodes 114 and 115 may be divided by the current applied through electrodes 112 and 113 to obtain an impedance measurement. Circuit 102 may determine impedance, resistance, reactance, phase and/or any other suitable property of the region. Based on the measured signal, electrical parameters, and/or electrical properties of the region of tissue, circuit 102 may determine a muscle characteristic. For example, circuit 102 may diagnose and/or assess a neuromuscular disease based on any suitable criteria, as discussed in further detail below.

In some circumstances, circuit 102 may display one or more of the determined electrical parameters to facilitate diagnosis and/or assessment by a physician or technician. Circuit 102 may include any suitable components for performing such measurements, calculations, determinations, and presentation functions. As one example, circuit 102 may include a lock-in amplifier for impedance measurement, a computer for performing calculations, and a display for displaying the results to a user (e.g., a technician, a physician, or a patient). However, it should be appreciated that any suitable components or combination of components may be used, as the invention is not limited for use with any particular components or configuration of the components.

Figure 2:
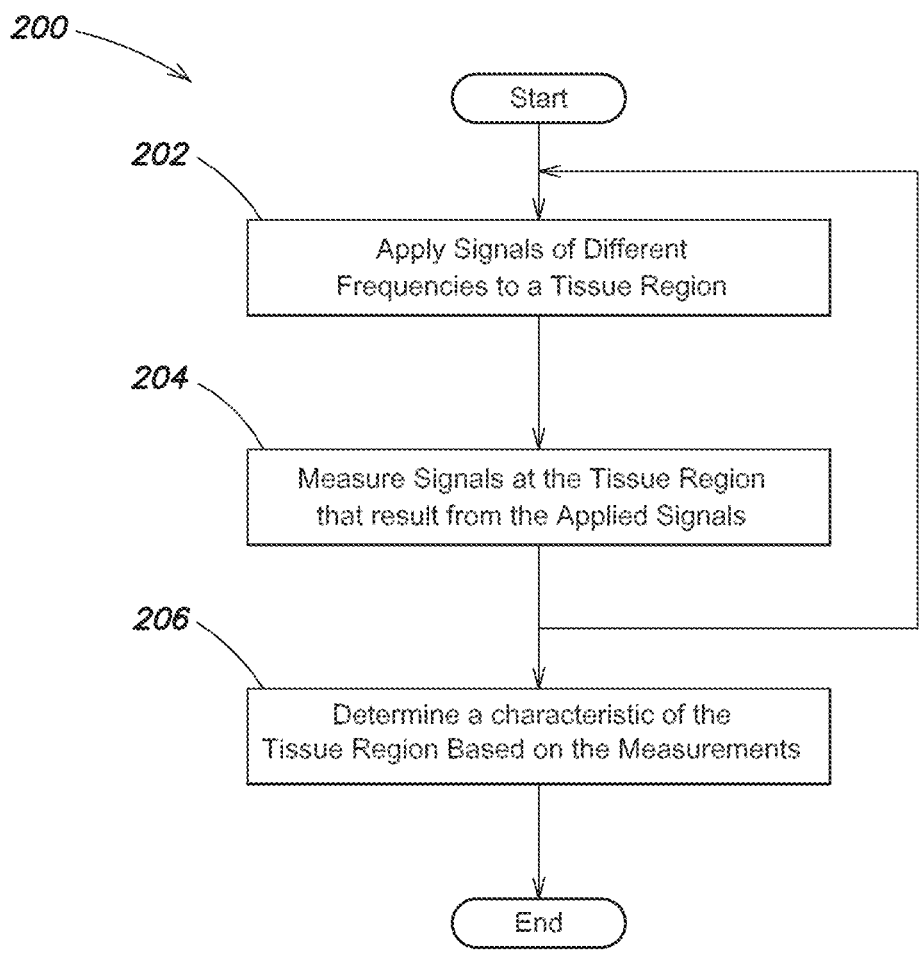
FIG. 2 is a flow chart illustrating a multi-frequency method of determining a characteristic of a tissue region of an organism, according to one embodiment.

FIG. 2 is a flowchart of a method 200 for performing multi-frequency EIM, according to one embodiment. As described above, a first signal of a first frequency is applied to a tissue region in step 202, and a first signal measurement is made in step 204, such that the measured signal is a result of applying the first signal of the first frequency. Next, a second signal of a second frequency is applied to the tissue region in step 202, and a second signal measurement is made for the second frequency in step 204. Further signals at different frequencies may also be applied, and corresponding measurements may be taken. Any suitable number of frequencies may be used in the multi-frequency EIM procedure, as the invention is not limited as to the number of frequencies measured or the exact frequencies at which measurements are taken. Preferably, if multi-frequency EIM is performed, the frequencies used should be of a number and value such that the measurements are sufficient to provide information useful in assessment or diagnosis of the tissue region, e.g., the assessment or diagnosis of a muscle condition.

In step 206, a characteristic of the region of tissue is determined based on the measurements. The characteristic that is determined may be a muscle characteristic, and may be determined based on one or more electrical properties obtained from the measurements, such as the impedance, phase, resistance and/or reactance of the muscle. As another example, a frequency-averaged impedance, phase, resistance and or reactance may be determined for at least a portion of the range of frequency measurement. The frequency-averaged parameter may be a useful parameter for comparing healthy vs. unhealthy tissue, and evaluating changes in the tissue over time. For example, a diagnosis of a neuromuscular condition may be made based on a frequency-averaged parameter being above or below a threshold value.

One or more electrical properties obtained from measurements taken from the region of tissue as a function of frequency may be used as a signature for the region of tissue. The term signature refers herein to any collection of information obtained from a region of tissue that is characteristic of the tissue. The signature of the tissue, once obtained, may be analyzed to assess, diagnose or otherwise determine a characteristic and/or condition of the region of tissue.

The signature of the tissue may be computationally processed and/or analyzed or presented to a physician or technician for analysis. As one example, a plot of an electrical parameter vs. frequency (e.g., resistance, reactance or phase of the tissue vs. frequency) may be displayed on a computer monitor, and a physician may make a diagnosis based on the plot displayed. Multiple plots displaying any of various electrical properties of the tissue with respect to frequency may be displayed, as the aspects of the invention are not limited in this respect.

Figure 3:
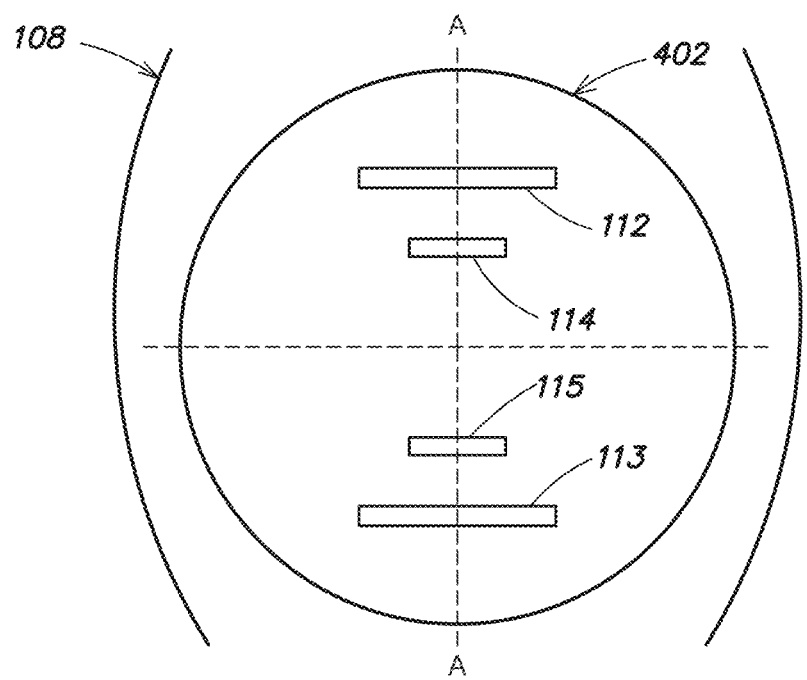
FIG. 3 is a diagram illustrating an example of a device that performs electrical impedance myography, according to one embodiment.

FIG. 3 is a diagram of an electrode array configured to perform EIM within a region of tissue 108. FIG. 3 show electrodes 112-115, as described above with respect to FIG. 1. Electrodes 112-115 may be mounted on a base 402. FIG. 3 illustrates performing EIM along a direction A-A aligned with an axis of the region of tissue 108, e.g., substantially aligned with fibers of the muscle. When a measurement is to be taken, electrodes 112-115 are brought into contact with the skin at the region of tissue, and are aligned in a direction with respect to an axis of the region. When performing multi-frequency EIM, current at different frequencies are applied at current-injecting electrodes 112 and 113, and resulting signals at the different frequencies are measured at electrodes 114 and 115.

Figure 4:
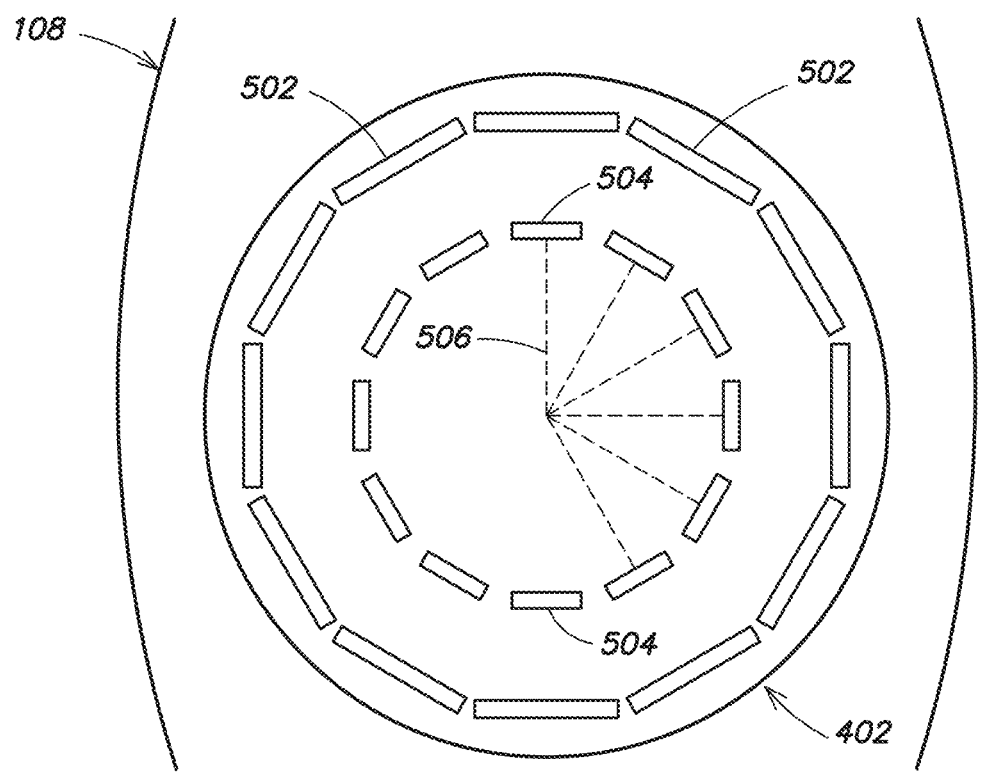
FIG. 4 is a diagram illustrating an example of a device that performs electrical impedance myography at a plurality of angles, according to one embodiment.

FIG. 4 illustrates another embodiment of an electrode array configured to perform EIM, in which a plurality of current-injecting electrodes 502 and voltage-measuring electrodes 504 are mounted on base 402 at different orientations. Since the electrodes are mounted at a plurality of different orientations, it may not be necessary to rotate the electrodes or base 402 to make measurements at different angles. When a first measurement is to be made, an appropriate pair of current-injecting electrodes can be selected and coupled to signal-generating circuit 106 using any suitable switches. That is, the plurality of electrodes may be configured such that the combination of electrodes 502 and 504 at any desired orientation may be selectively activated.

For example, the current-injecting electrodes that lie along line 506 may be selected first. Additionally, the appropriate pair of voltage measuring electrodes 504 that lie along line 506 may be selected, and may be coupled to signal-measuring circuit 104 using any suitable switches. A first measurement may then be taken along direction 506. When a measurement is to be made along a different direction, the switches may be reconfigured to couple different electrodes 502 and 504 to the appropriate circuits, and measurement may be taken at a different orientation.

Figure 5:
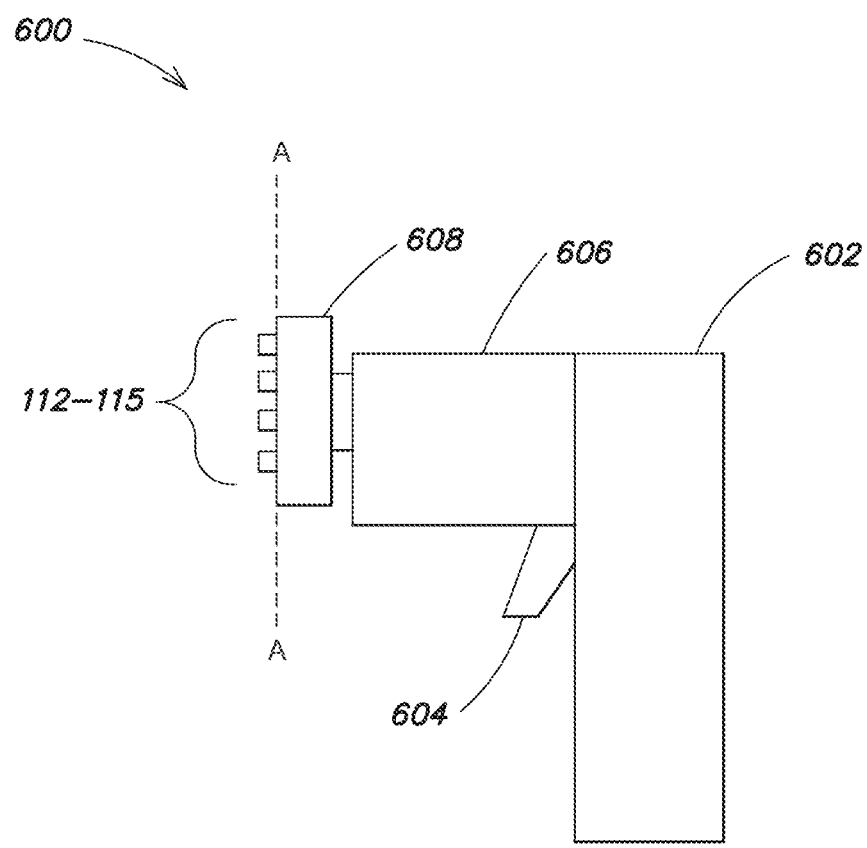
FIG. 5 is an example of a device for that performs electrical impedance myography measurements.

FIG. 5 illustrates an example of a hand-held apparatus 600 that may be used for performing EIM, including rotational and/or multi-frequency EIM. Providing a hand-held EIM device may facilitate making EIM measurements, and thus may reduce the amount of time needed to make the measurements. Hand-held apparatus 600 may include a handle 602, a user interface 604, a body 606, base 608 and electrodes 112-115. The electrodes may be coupled to circuit 102 in any suitable way, such as through a cord attached at the bottom of handle 602, for example. FIG. 5 illustrates direction A-A corresponding to direction A-A illustrated in FIG. 3.

In one embodiment, base 608 may be rotatable, as discussed above, for performing rotational EIM. In another embodiment, base 608 may not be rotatable, but may have a plurality of electrodes 502 and 504 positioned at different orientations, as described in connection with FIG. 4. Apparatus 600 may be configured such that either technique may be used, depending on the type of base/electrode combination that is mounted to the apparatus. In some circumstances, it may be desirable to provide multiple different base/electrode combinations of different sizes that may be easily interchangeable for measuring different types of muscles, or muscles of different sizes. When a different size is needed, the base 608 may be detached from apparatus 600 and another base may be attached.

Figure 6:
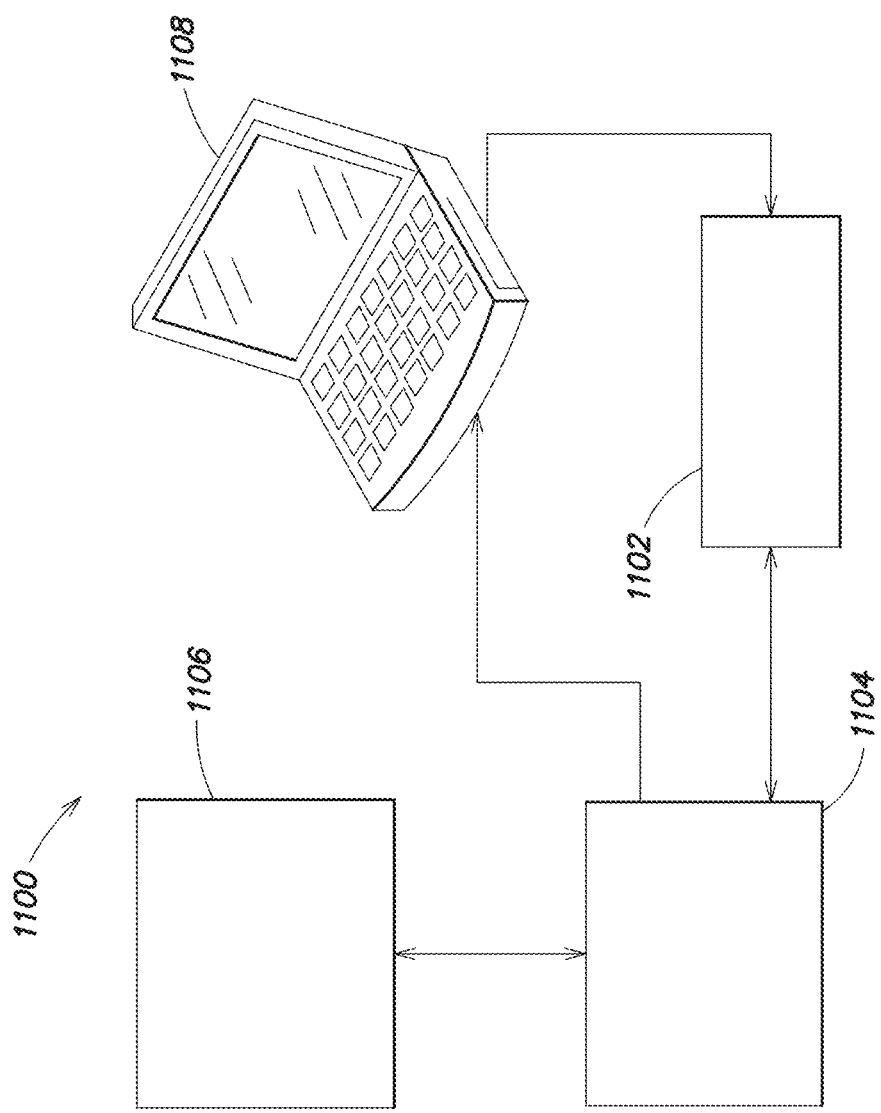
FIG. 6 is a schematic block diagram of an EIM measurement system, according to some embodiments.

In some embodiments, the EIM measurement system may comprise, as shown schematically in a system 1100 in FIG. 6, a signal generator 1102, a crosspoint switch network 1104, an electrode array 1106, which may be reconfigurable, and a data acquisition module 1108. Electrode array 1106 may be reconfigurable electronically, manually, or in any other suitable manner. System 1100 may comprise any other suitable components as well, as discussed in more detail below. Electrodes of the electrode array may be located on a head of a portable device. In the array, neighboring electrode elements (e.g., vias, pins, solder pads or other elements) may be connected together (e.g., electrically) to create a so-called "composite electrode." In such an arrangement, multiple electrodes may act as a single unit which may be used for signal excitation (e.g., current-injecting) or pickup (e.g., voltage-measuring). Furthermore, at each configuration of the multiple electrodes, a signal comprising multiple frequencies may be applied to muscle tissue.

In some embodiments, the excitation (e.g., current-injecting) electrodes and pick-up (e.g., voltage-measuring) electrodes of the electrode array may be reconfigurable automatically. Thus, one or more combinations of the electrodes that provide sufficiently high resolution of measurements of the muscle anisotropy may be selected automatically.

In addition, in some embodiments, it may be detected that one or more of the electrodes of the electrode array do not contact the surface of the skin of the region being analyzed well enough for these "faulty" electrodes being used in impedance measurements. Accordingly, the electrode array may be reconfigured so that these "faulty" electrodes are not used in the impedance measurements.

Figure 7:
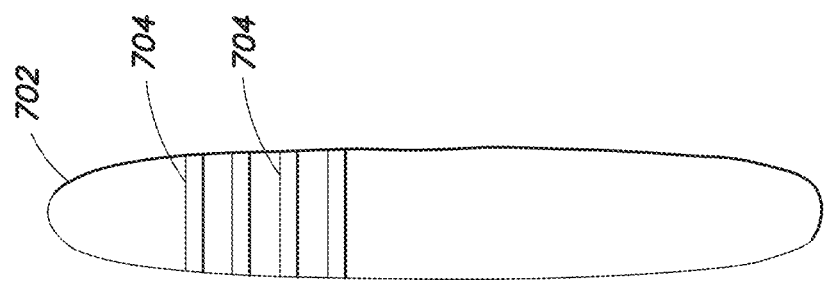
FIG. 7 is a diagram illustrating an example of a device that performs electrical impedance myography, according to one embodiment.

Some embodiments relate to an apparatus configured to perform EIM measurements on an individual's tongue. In such an apparatus, an array of electrodes may be positioned on a device capable of being inserted into a person's mouth where the array of electrodes may be configured to contact a surface of the tongue. An exemplary device is illustrated in FIG. 7 consisting of four electrodes 704 configured on an implement 702 such as a tongue depressor or coffee stirrer. Wires connected to the electrodes in the electrode array may be configured to supply an electrical signal and/or measure a response electrical signal. As an example, the outer electrodes on the array may be configured as current-injection electrodes and the inner electrodes may be configured as voltage-measuring electrodes.

In some embodiments, the electrode array may be configured to perform multi-directional EIM measurements and have multiple electrodes at different orientations, such as depicted in FIG. 4, to obtain EIM measurements with respect to different alignments with the region of tissue, in this case an individual's tongue. Such a device configured to perform multi-directional EIM may have the current-injecting electrodes positioned on as outer electrodes and the voltage-measuring electrodes as inner electrodes.

In some embodiments, an electrode array may connect with another device such that electrical contacts of the electrode array are configured to contact electrical contacts of the device when connected. The device may be configured to provide and receive electrical signals from the electrode array such that the combination of the electrode array connected to the other device may perform EIM measurements. For example, the electrode array shown in FIG. 7 may be configured to connect with an integrated device by inserting implement 702 into the integrated device in order to perform EIM measurements. By replacing the electrode array, the integrated device may be used to perform EIM measurements on multiple individuals without having to reuse the same electrode array. Such techniques may be advantageous by allowing a sterile electrode array to be used per each individual.

Such a device may be configured to perform EIM measurements on an individual's facial muscle may be used to assess a condition of a facial muscle. For example, a device may be configured to perform EIM measurements on an individual's tongue to assess a condition of the tongue (e.g., tongue endurance). The condition of a facial muscle may be used to assess the onset of disease and/or progression of disease such as ALS. EIM measurements may correlate with other assessment measures of the severity of a disease. In some embodiments, the phase value obtained through EIM measurements may correlate with the health and/or a disease state of the muscle of an individual's tongue and may provide an indication of the health of the individual. For example, individuals diagnosed with ALS may show signs of bulbar impairment and EIM measurements may be used as a biomarker of bulbar health. Individuals with ALS show signs of bulbar impairment (e.g., tongue fasciculations, atrophy, weakness) and severity of disease (e.g., ALS Functional Rating Scale-R, bulbar subscore, speaking rate during reading task) and tongue function (maximum strength and endurance) may correlate with EIM impedance values. As an illustrative example, individuals with ALS can be found to have significantly smaller phase values than for healthy individuals without symptoms of ALS. For example, health individuals may have a phase value of approximately 16°, while individuals with ALS may have a phase value of approximately 10. Such techniques may be used to asses any condition where the tongue is affected including primary muscle disorders (e.g., oculopharyngeal muscular dystrophy), stroke, Parkinson's disease, and trauma.

Some embodiments relate to methods and apparatus for performing multi-frequency EIM measurements to improve analysis of EIM measurements by reducing the contribution of fat within the region of tissue in the electrical EIM data. By reducing signal contributions due to fat, the specificity of EIM as a tool for non-invasive assessment and diagnosis of muscle may be improved. In some embodiments, a ratio or difference of phase values obtained at two frequencies of applied electrical current provides a measure of muscle condition that is only minimally impacted by subcutaneous fat.

Since the frequency dependence of the material properties of muscle and fat (e.g., subcutaneous fat, intramuscular fat) may differ, EIM measurements may indicate this frequency dependence of the material properties that comprise a tissue being measured. Muscle generally has peak chargeability at between 50 and 100 kHz. In contrast, chargeability of fat increases continuously as frequency increases. Thus, at 50 kHz, both fat and muscle are contributing to the measured permittivity of the tissue. At 200 kHz, mainly fat is contributing to the measurement. Thus by taking a ratio, it is possible to reduce contribution of fat from the measurement because there is a differing contribution of fat at these different frequencies. Although frequencies of 50 kHz and 200 kHz are provided as an example, any suitable frequencies may be used to perform EIM measurements such that the contribution of fat in a measurement is reduced.

Figure 8:
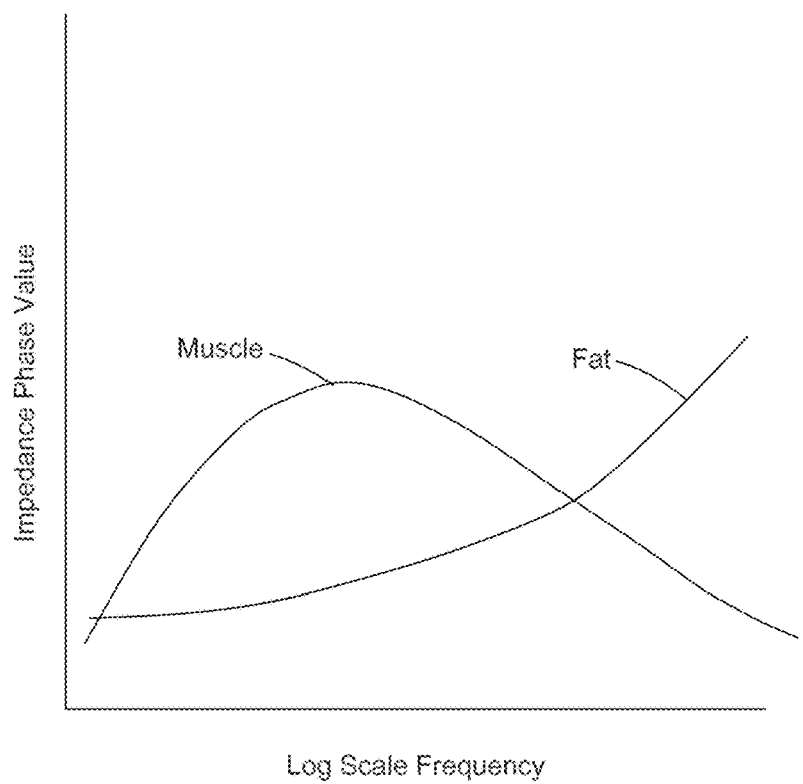
FIG. 8 is a plot of impedance phase value as a function of frequency for muscle and fat.

At some frequencies, muscle and/or fat may dominate an EIM measurement. As an example, FIG. 8 illustrates the frequency dependence of phase impedance measurements on muscle and fat. The phase value for muscle peaks at a lower frequency than the phase value for fat. Frequencies may be selected for impedance measurements with more significant contributions from fat or muscle. In some embodiments, the two frequencies may be at approximately 50 kHz and approximately 200 kHz, and a ratio or difference of impedance values may be calculated at these two frequencies. In some embodiments, the frequency ratio may include a numerator based on an approximate peak in the reactance as a function of frequency and denominator based on a frequency higher than the frequency associated with the approximate peak in the reactance. By comparing phase values taken at two frequency values, such as by taking a ratio or difference of the two values, may provide an approach to remove the impact of fat on interpretation of EIM measurements. Reducing the impact of fat on EIM measurements can be advantageous while tracking the progress of a disease and/or effectiveness of a treatment of a disease, since some therapies, such as corticosteroids, may alter subcutaneous fat. In addition, reducing the impact of fat on EIM measurements can assess an exercise routine by determining if an individual's muscle condition and/or quality is improved and if the individual is losing fat from the exercise routine.

Figure 9:
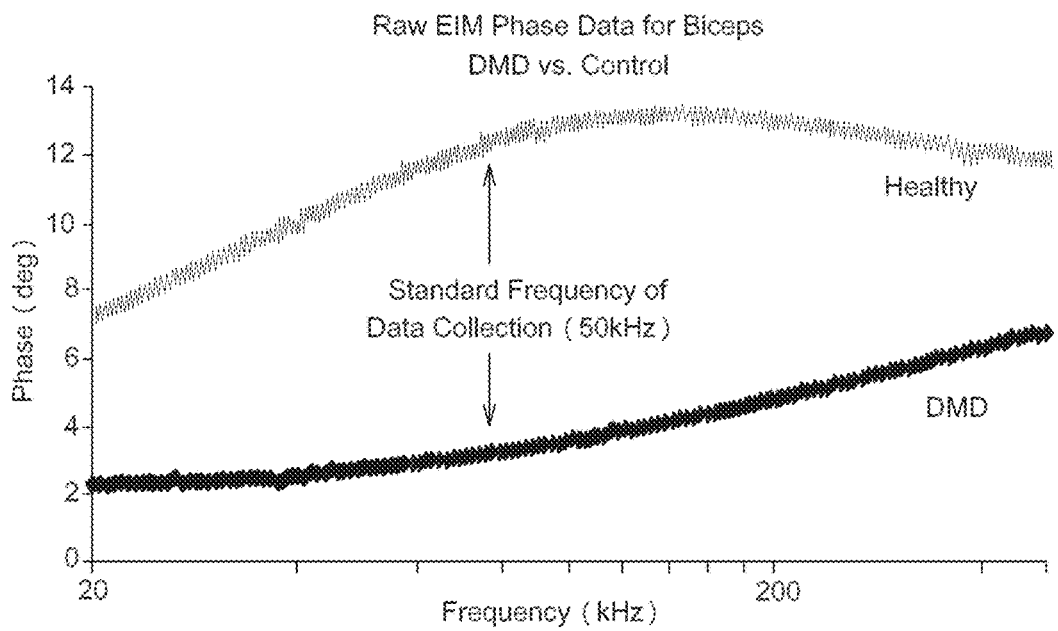
FIG. 9 is a plot of phase as a function of frequency for health and Duchenne muscular dystrophy (DMD) individuals.

As an illustrative example, EIM measurements performed on individuals with Duchenne muscular dystrophy (DMD) are compared to health individuals. FIG. 9 illustrates EIM phase data versus frequency for an individual with Duchenne muscular dystrophy (DMD) and a health individual.

Figure 10A:
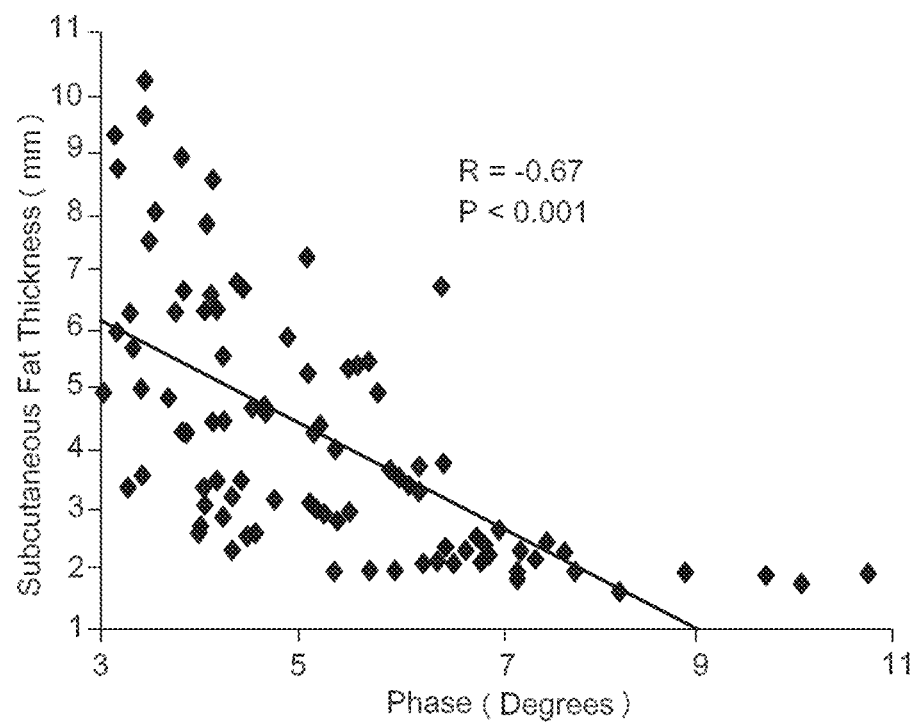
FIGS. 10A-B are plots of subcutaneous fat thickness and six minute talk distance as a function of phase.
Figure 10B:
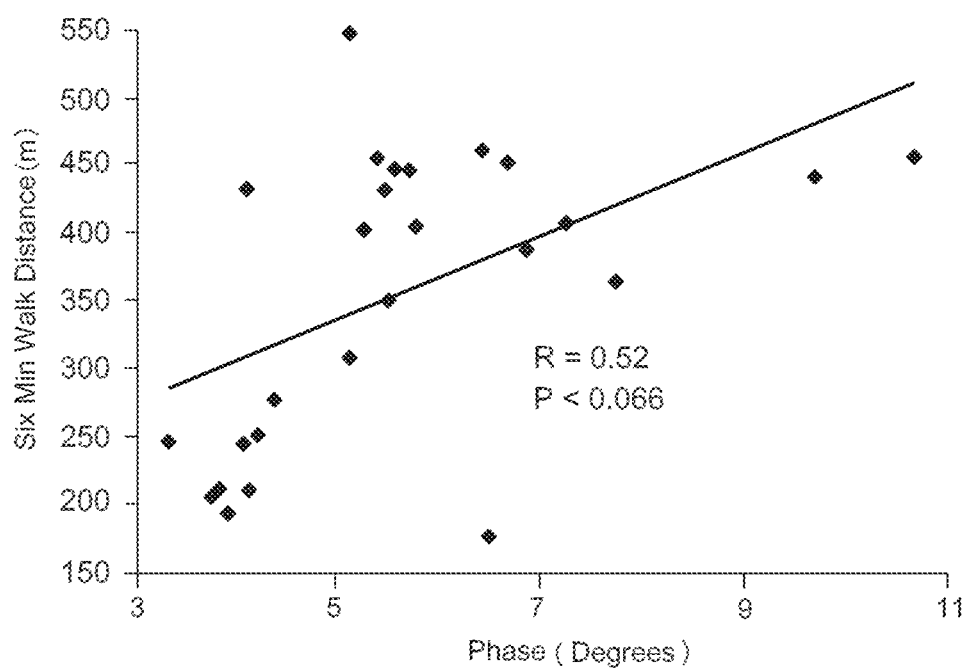
Figure 11A:
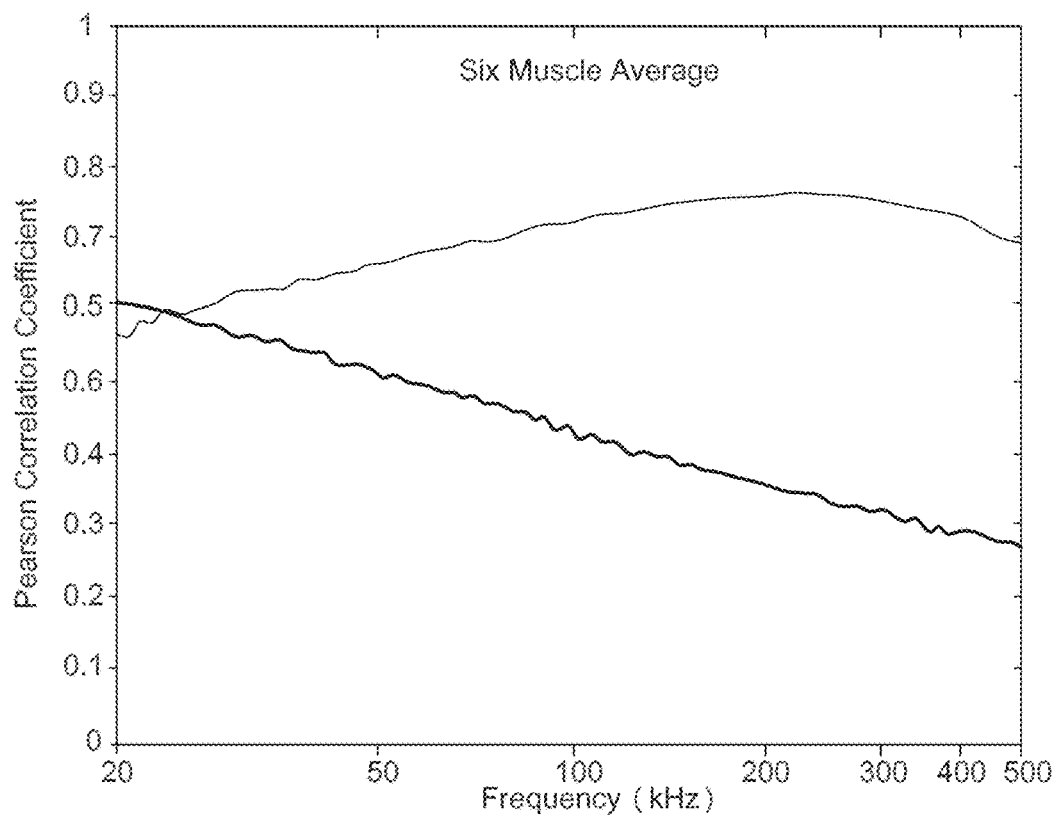
FIGS. 11A-B are plots of correlation coefficients of phase for six minute walk and subcutaneous skin fat thickness as a function of frequency and frequency ratio denominator for EIM measurements performed on six muscles.
Figure 11B:
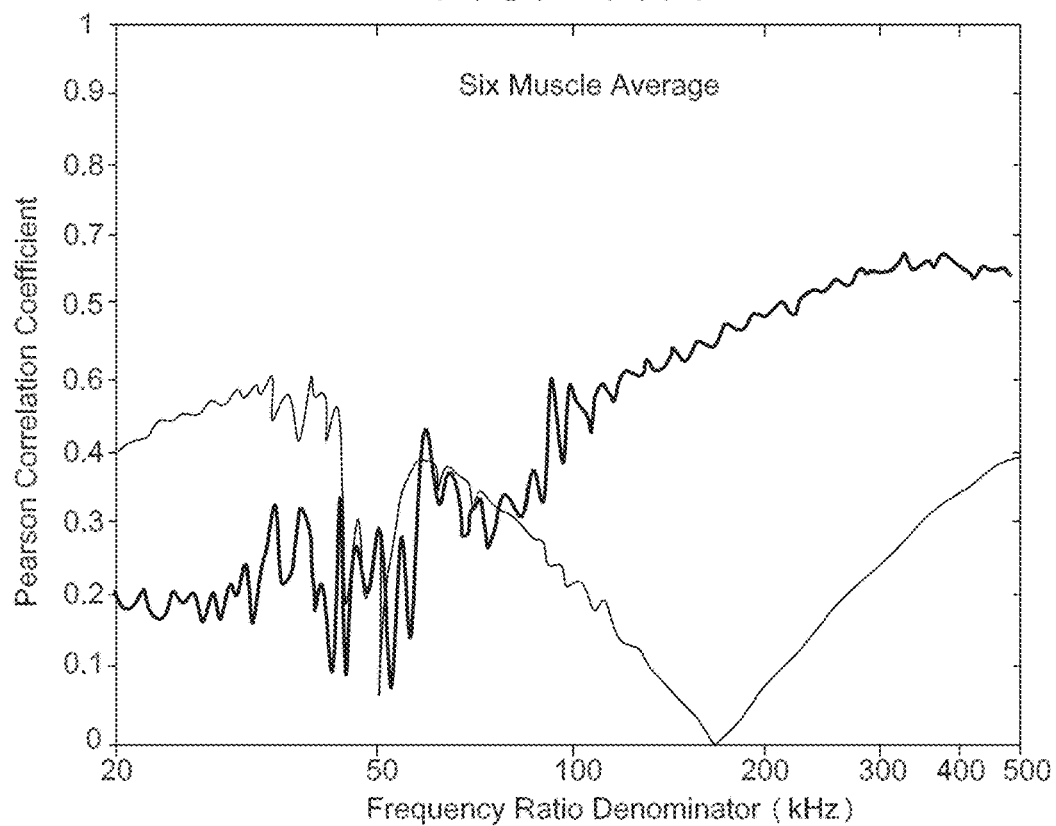
Figure 12A:
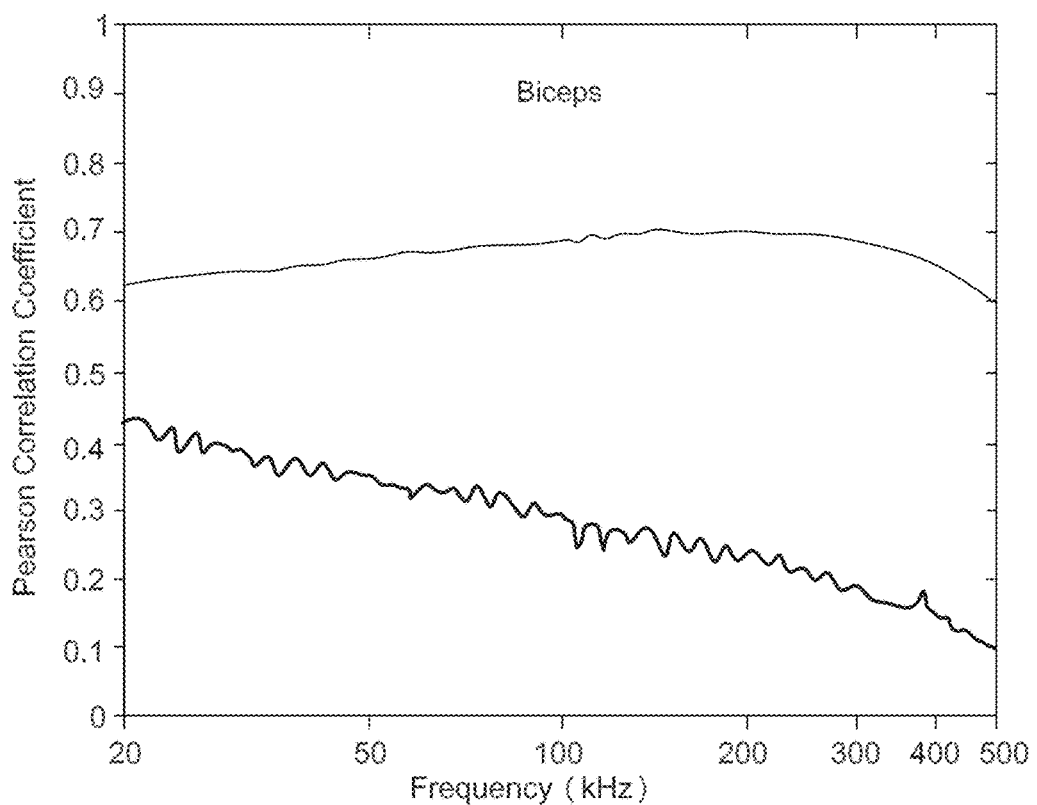
FIGS. 12A-F are plots of correlation coefficients of phase for six minute walk and subcutaneous skin fat thickness as a function of frequency and frequency ratio denominator for EIM measurements performed on individual muscles.
Figure 12B:
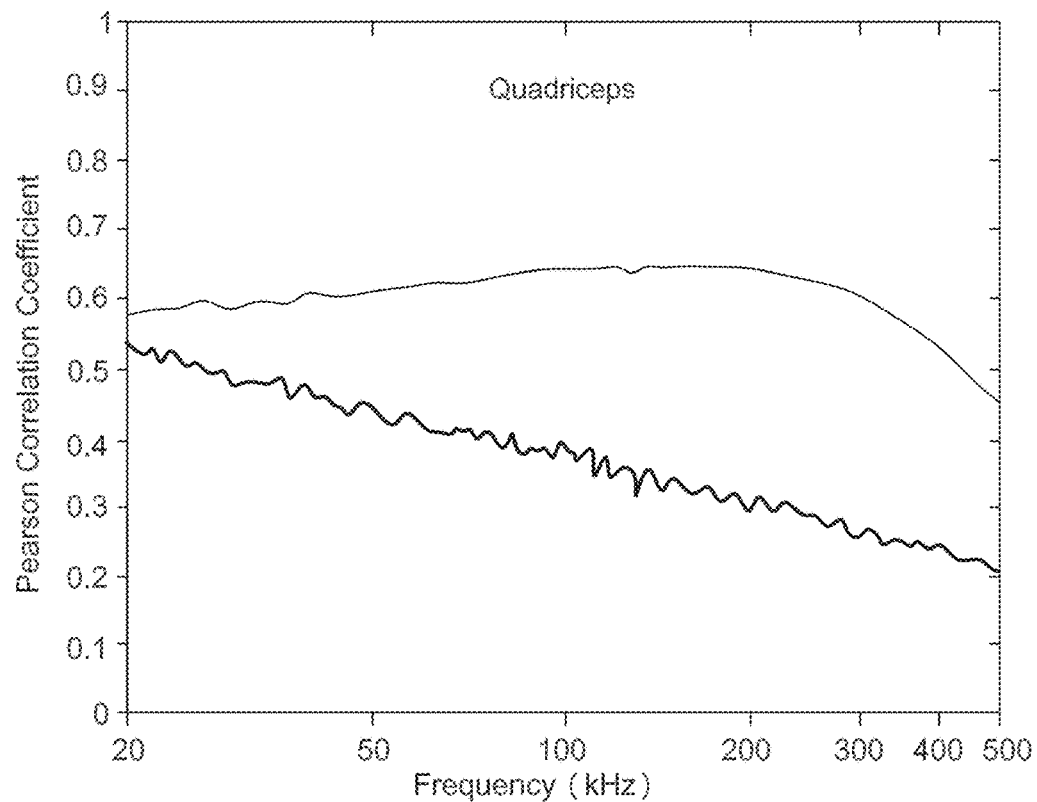
Figure 12C:
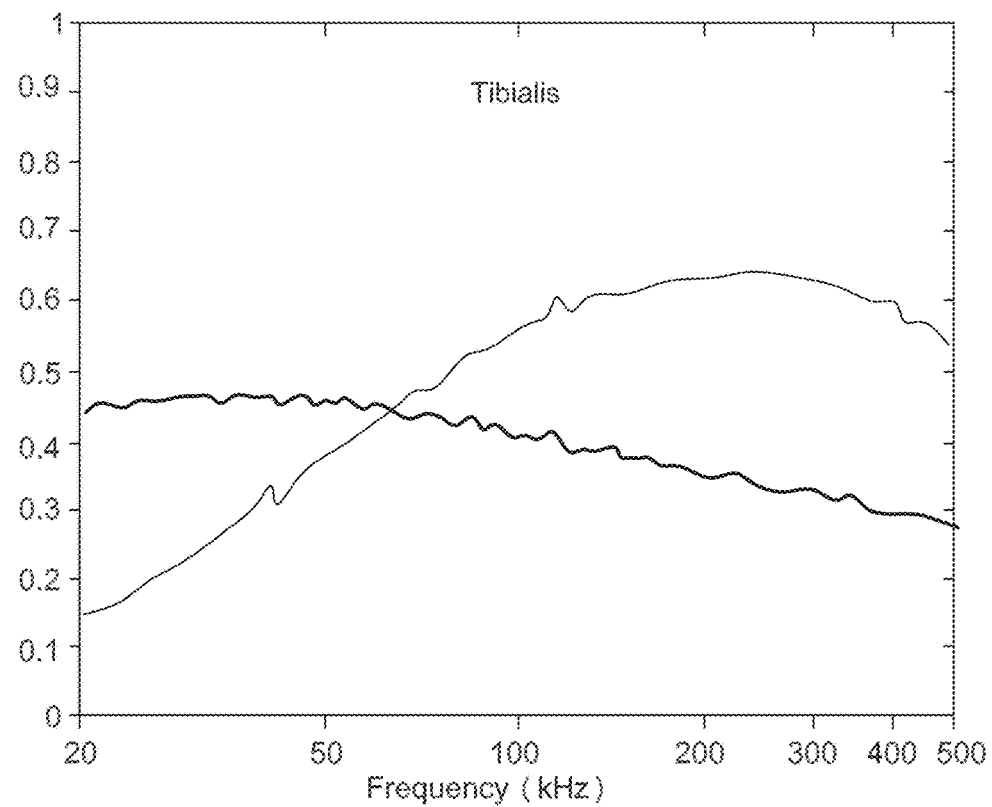
Figure 12D:
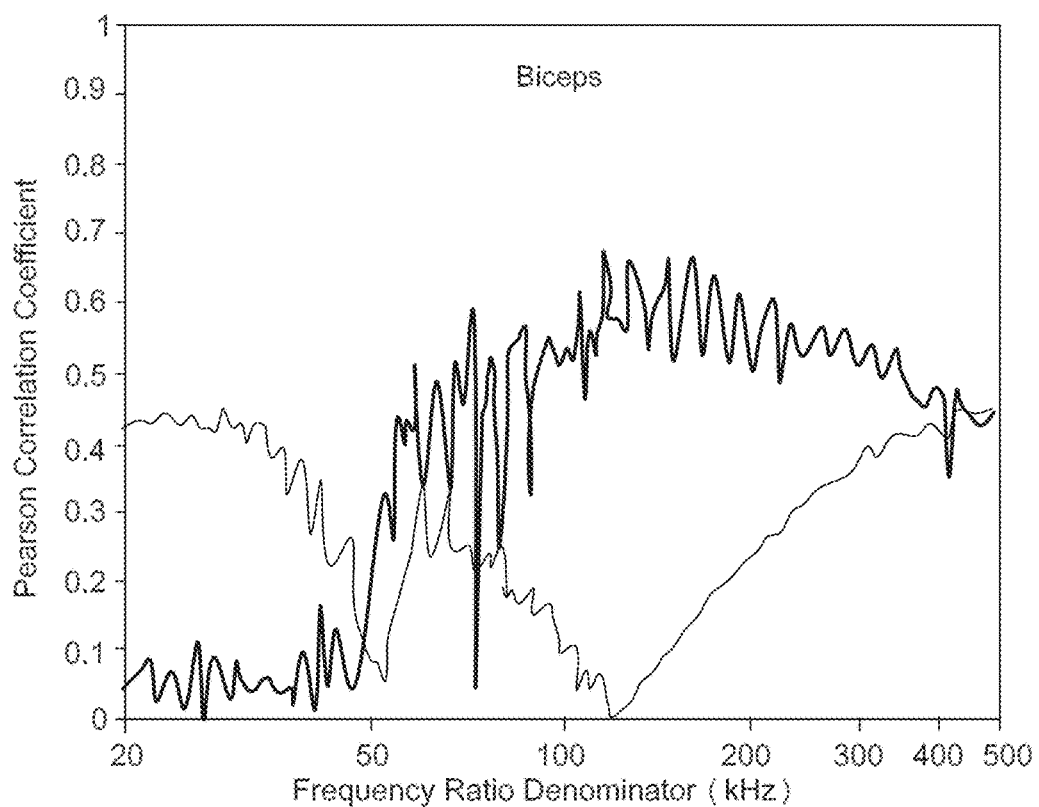
Figure 12E:
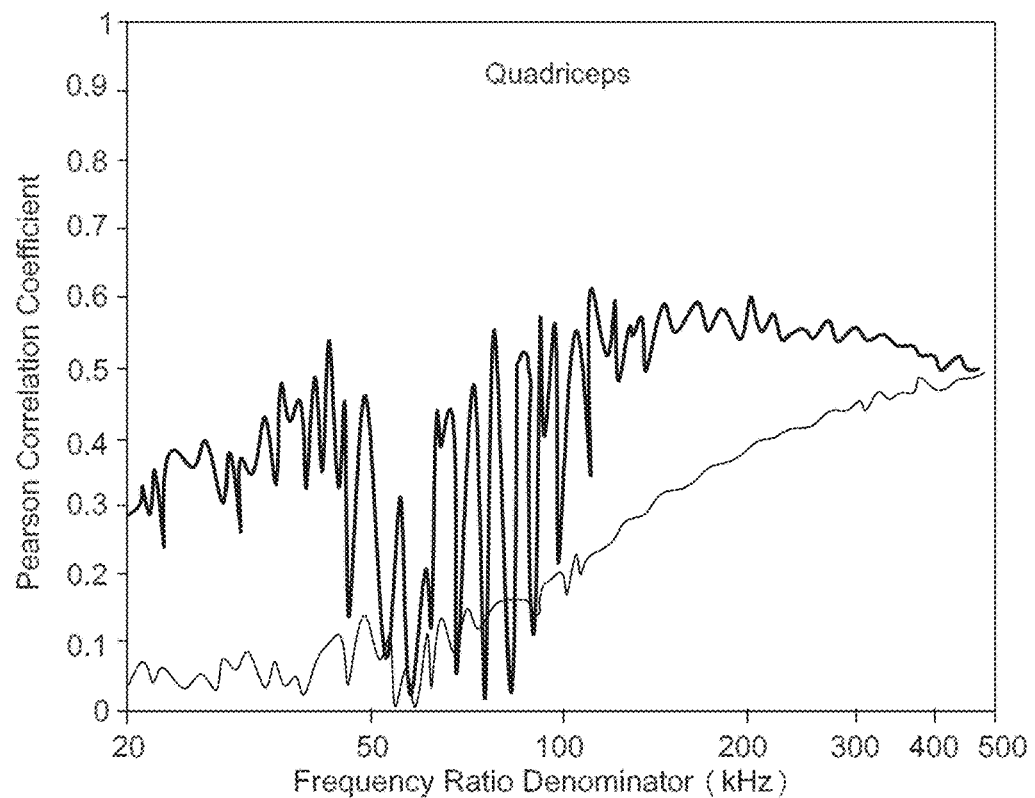
Figure 12F:
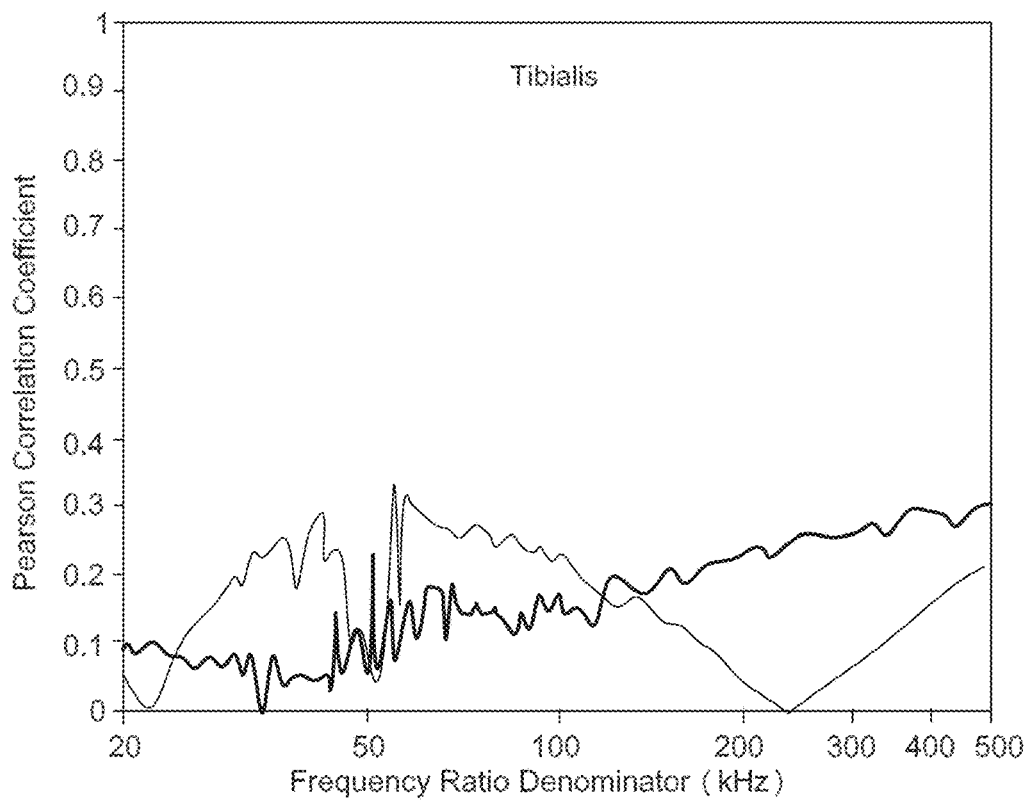
Figure 13A:
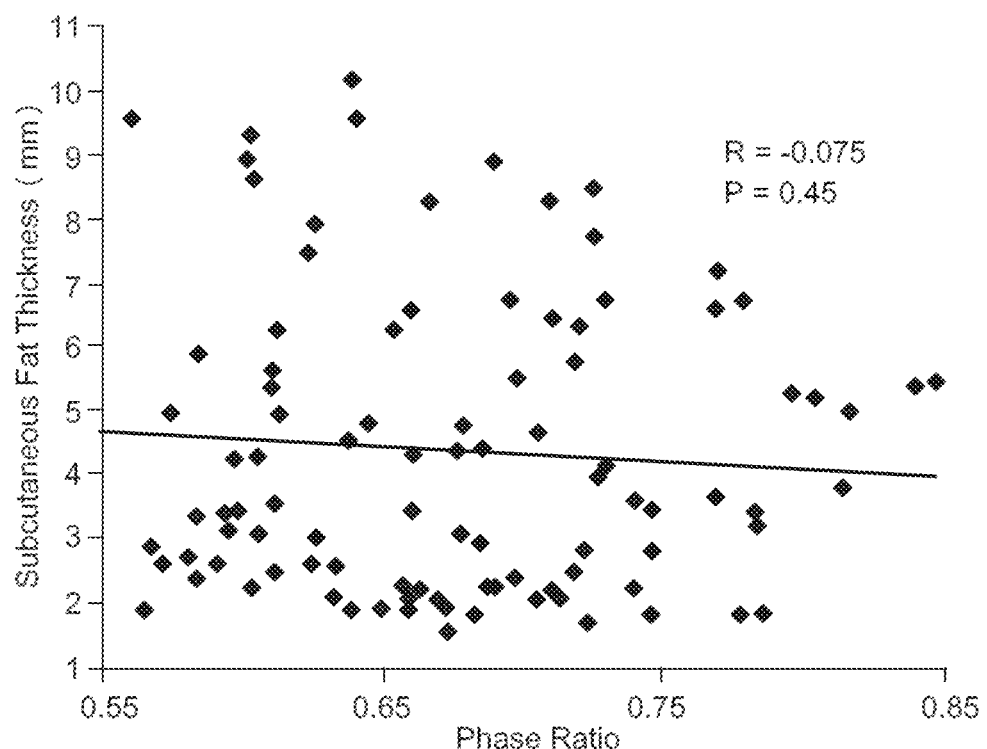
FIGS. 13A-B are plots of subcutaneous fat thickness and six minute talk distance as a function of phase.
Figure 13B:
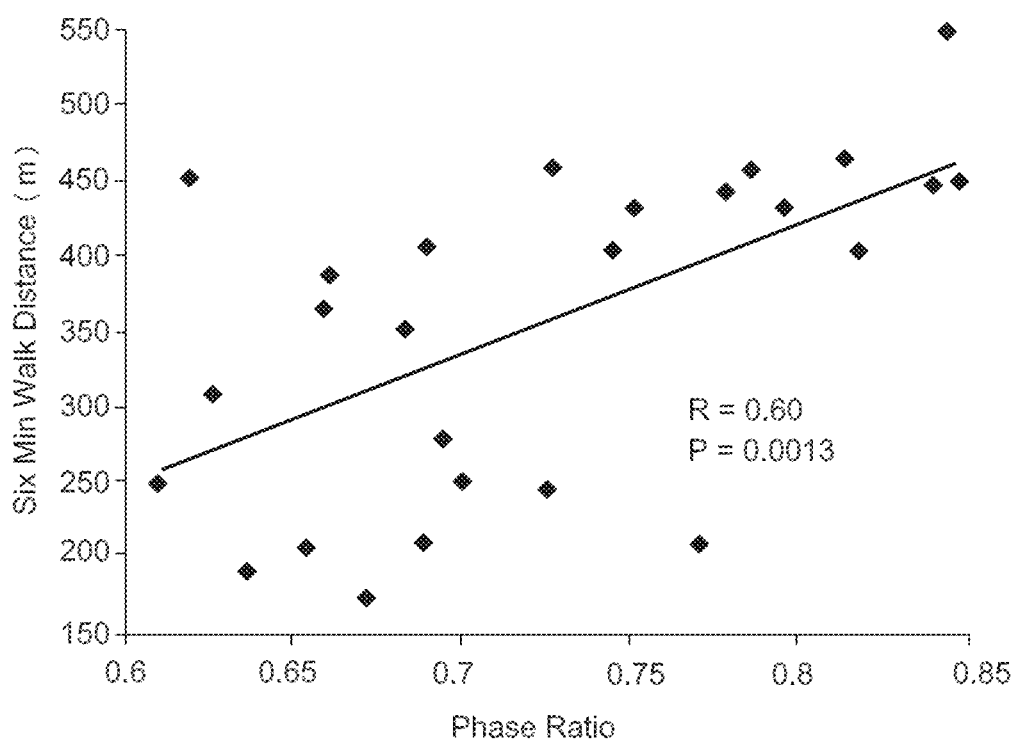
Figure 14A:
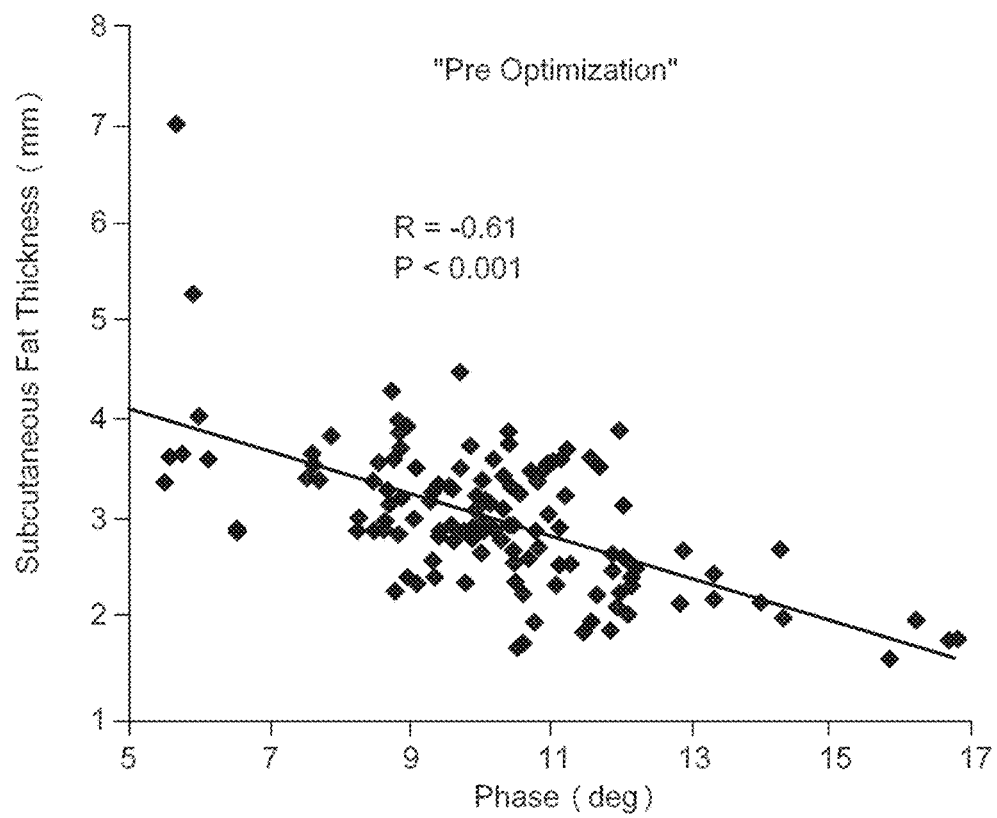
FIGS. 14A-B are plots of subcutaneous fat thickness and six minute talk distance as a function of phase pre-optimization.
Figure 14B:
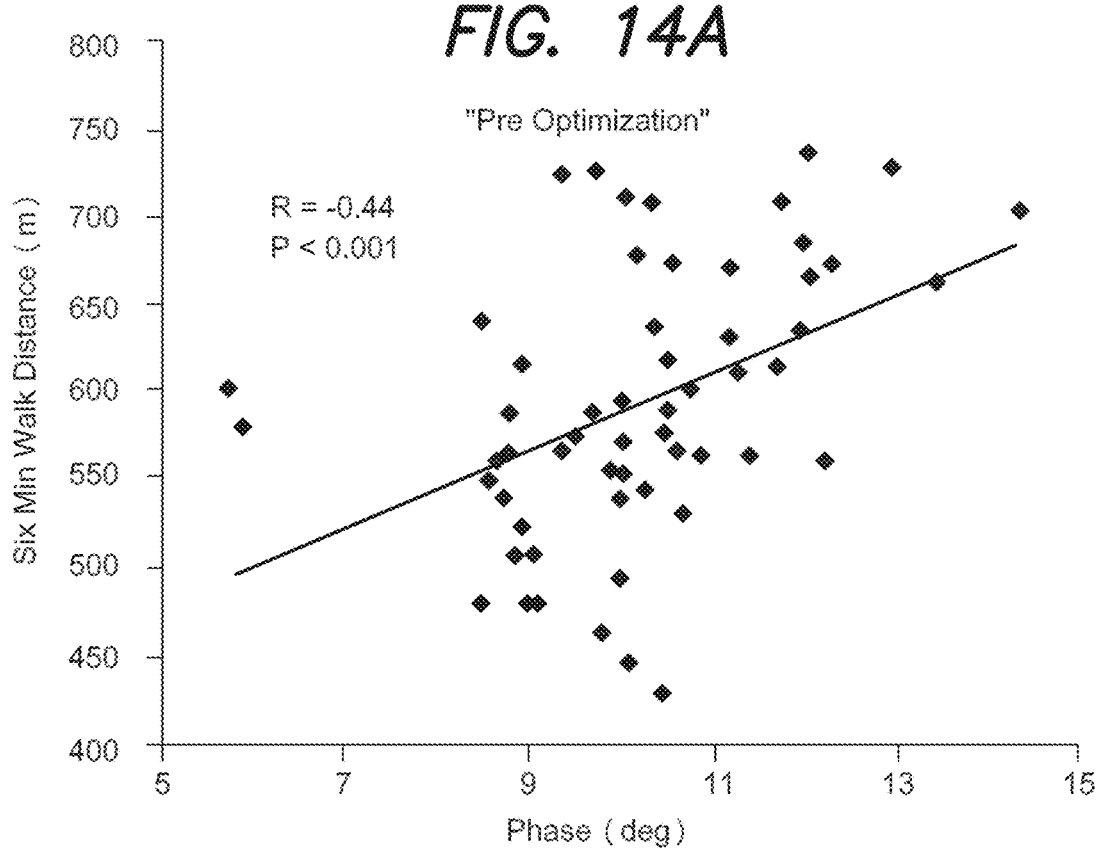
Figure 15A:
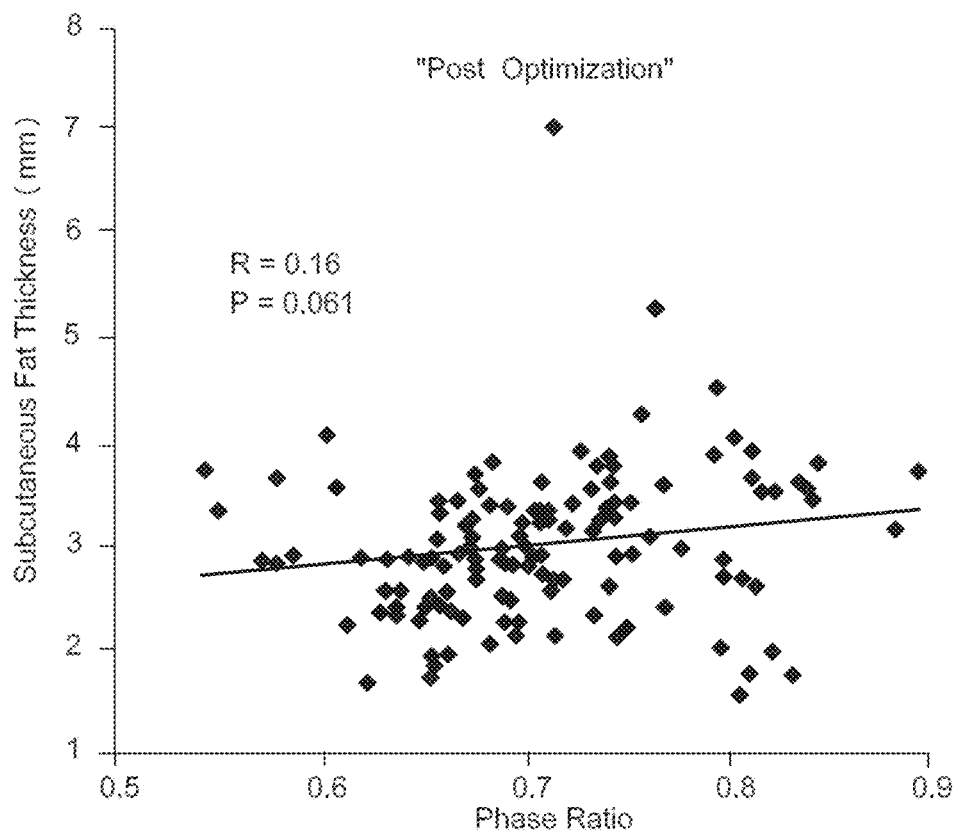
FIGS. 15A-B are plots of subcutaneous fat thickness and six minute talk distance as a function of phase post-optimization.
Figure 15B:
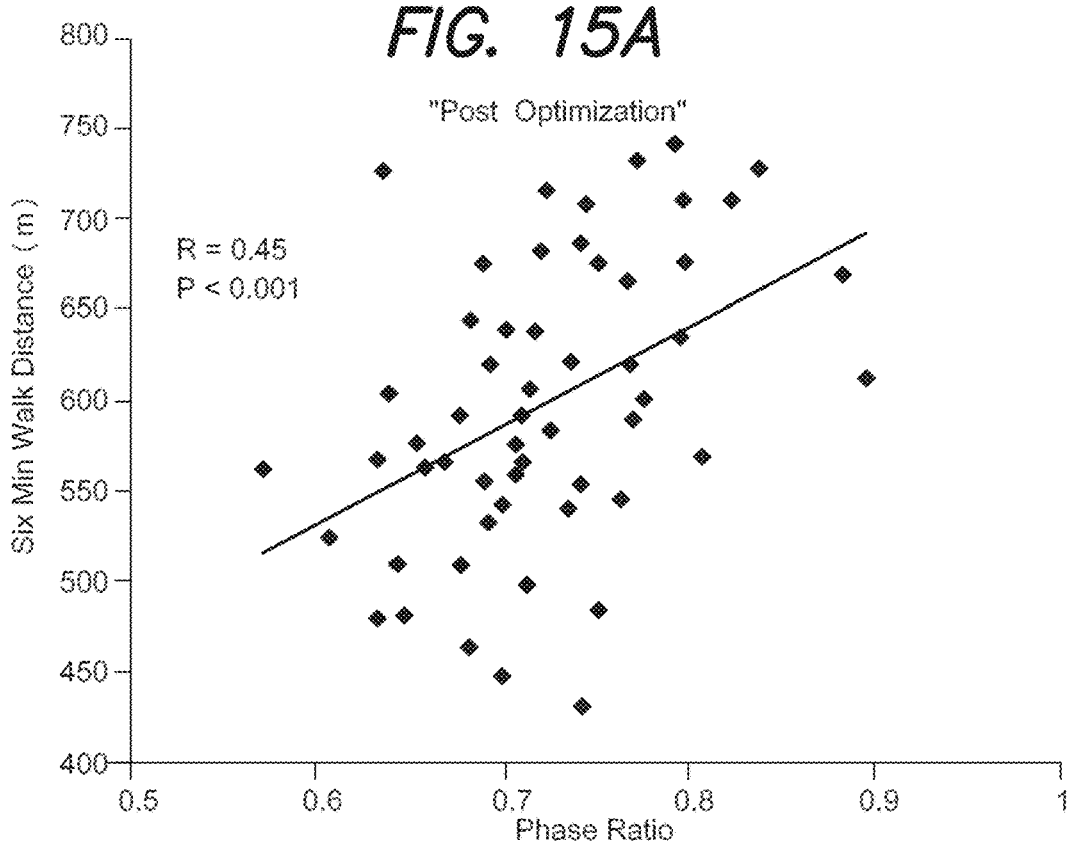

Selection of two frequencies may be determined using any suitable manner. In some embodiments, one impedance parameter value may be held at one frequency while other frequency changes in order to identify a suitable ratio or difference. As an example, a range of ratios may be obtained by maintaining the 50 kHz EIM data in the numerator and by placing in the denominator a range of values starting at 20 kHz and extending up to 500 kHz, plotting absolute values of the correlation coefficient (R) versus the denominator frequency values for a six minute walk test (6MWT) and subcutaneous fat (SF) thickness. The ratio and 50 kHz raw data were then applied to the baseline data from healthy boys to see how much the SF thickness-EIM correlation decreased across that population of individuals and whether it reduced coefficient of variation in the raw data. FIG. 10A shows the respective relationship between EIM 50 kHz phase 6-muscle average and 6MWT data in all 26 visits of the 13 boys. FIG. 10B illustrates a relatively strong correlation between EIM 50 kHz phase and SF thickness measured at the same time. FIGS. 11 and 12 show the frequency optimization curve for a 6-muscle average data set and several individual muscles, respectively. In FIG. 11, the lines represent correlation coefficients of phase versus six minute walk (black), and phase versus subcutaneous skin fat thickness (gray) at correlations of raw EIM phase data from 20 to 500 kHz (FIG. 11A) and correlations of EIM phase ratio as a function of frequency (FIG. 11B). FIG. 12 shows optimization curves for single muscle EIM phase data where black lines represent the correlation coefficient of phase to 6MWT and gray lines represent the correlation coefficient of phase to subcutaneous skin fat thickness at correlations of raw EIM phase data from 20 to 500 kHz (FIGS. 12A-C) and the phase ratio denominator frequencies (FIGS. 12D-F). As illustrated in FIG. 12, in the region of 200 kHz, the R value for SF reaches a minimum at the same time the R value for 6MWT is nearly maximized. FIG. 13A-B illustrates similar plots as shown in FIG. 10A-B but using the optimized phase 50/200 ratio, demonstrating that the correlation with the 6MWT is strengthened while dramatically reducing the impact of the SF thickness to the point that it becomes non-significant. An additional example of correlation values pre-optimization and post-optimization are shown in FIGS. 14A-B and 15A-B.

Although a ratio of phase values are discussed with respect to the above example, a similar technique may be used to remove the contribution of fat signal on other impedance measures such as reactance or resistance. Additionally, as illustrated in FIGS. 13, 14, and 15, comparing between two impedance metrics at different frequencies to reduce the contribution of fat may be performed across a population of individuals.

One or more electrical parameters may be indicative of a structural component or feature of the muscle such as a fiber size of the muscle. The fiber size may be an approximate fiber size, an average fiber size, and/or a relative fiber size of the fibers that comprise the muscle. The fiber size may then provide information for assessing and diagnosing the muscle's condition such as for evaluating effects of exercise, disuse of a muscle on the muscle's health, disease progression, and/or response to therapy. In some embodiments, a value of a peak frequency may be obtained through multi-frequency EIM measurements and used to indicate a fiber size of a muscle. The peak frequency may be obtained from reactance and/or phase as a function of frequency.

Figure 16:
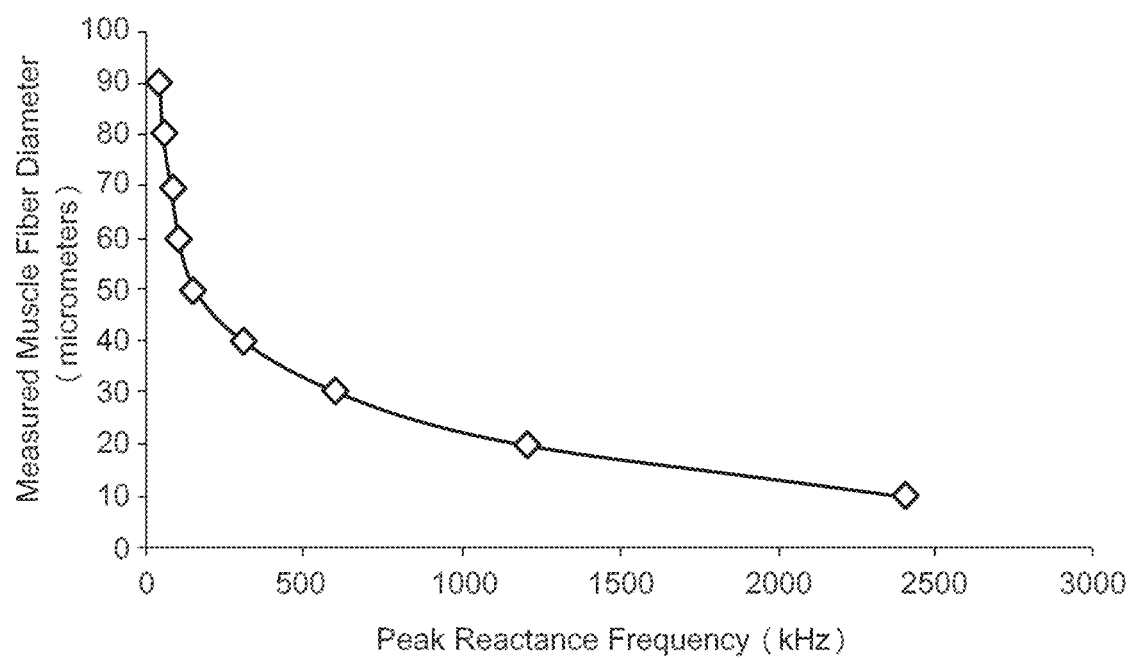
FIG. 16 is a plot of muscle fiber size as a function of peak reactance frequency.

Multi-frequency EIM measurements performed on one or more muscles with a known fiber size may indicate a correlation between a peak frequency and fiber size. A relationship between fiber size and peak frequency may be found in any suitable way. For example, muscle cross-sectional sizes may be measured from series of samples of muscle of varying fiber size such as tissues obtained from mouse, rat, pig or cow. Such measurements on the series of tissues may be performed through standard quantitative microscopy techniques. EIM measurements performed on a muscle may determine a peak frequency from an electrical parameter determined by the EIM measurements as discussed above. As measurements are performed on the series of muscle samples with known fiber size, a relationship between peak frequency and fiber size may be obtained. An illustrative example of peak reactance frequency and associated muscle fiber size are plotted in FIG. 16 and provided in the table as follows:

| Measured peak reactance frequency | Associated muscle fiber size |
|---|---|
| 40 kHz | 90 μm |
| 41 kHz | 89 μm |
| 42 kHz | 88 μm |
| 43 kHz | 87 μm |
| 44 kHz | 86 μm |
| 45 kHz | 85 μm |
| 46 kHz | 84 μm |
| 47 kHz | 83 μm |
| 48 kHz | 82 μm |
| 49 kHz | 81 μm |
| 50 kHz | 80 μm |
| 51 kHz | 79 μm |
| 52 kHz | 78 μm |

By obtaining a function of peak frequency values associated with known fiber size, a peak frequency corresponding to an unknown fiber size may be used to identify an unknown fiber size of a muscle. Additionally, a look-up table relating peak reactance value to fiber size may be provided such as the preceding table. When multi-frequency EIM measurements are performed on a region of tissue a peak frequency may be obtained from these measurements and can be used to identify a corresponding fiber size either through the look-up table and/or the function of muscle fiber size versus peak frequency. In some instances a peak frequency may be obtained by evaluating a peak frequency value of reactance as a function of frequency and/or phase as a function of frequency.

The peak frequency may decrease as muscle fibers become larger. For example, in a healthy individual who is extremely fit, a reactance peak frequency may be approximately 40 kHz and correspond to an average muscle fiber size of 90 μm. In contrast, in an individual who is healthy but not well conditioned, the peak frequency may be 65 kHz, which may correspond to a muscle fiber size of 71 μm. While in a person with a muscle disease, a peak frequency of 600 kHz corresponding to a muscle fiber size of 30 μm may be found. These techniques allow for the identification of the size of the muscle fibers non-invasively by using impedance techniques and the relationship of peak frequency values to known muscle fiber size.

In some embodiments, a Col-Cole impedance model may be used to determine one or more impedance model parameters from EIM measurements. Multi-frequency EIM measurements may be performed over a certain range of frequencies and resistance $R(\omega)$ and reactance $X(\omega)$ spectra are obtained across the frequency range. From the resistance and reactance, the muscle conductivity $\sigma(\omega)(S \cdot m^{-1})$ and the relative permittivity $\varepsilon_r(\omega)$ may be obtained. In some embodiments, the muscle conductivity and relative permittivity may be determined based on the configuration and arrangement of the EIM probe with the region of tissue.

The complex resistivity $\rho(\omega)$ may be calculated from the muscle conductivity and relative permittivity over the frequency range. In some embodiments, the complex resistivity may be found using the following equation:

$$\rho(\omega) = \frac{1}{\sigma(\omega) + j\omega\varepsilon_0\varepsilon_r(\omega)}$$

The calculated complex resistivity based on the EIM measurements may be fitted to an impedance model. In some embodiments, the Cole-Cole impedance model may be fitted to the complex resistivity over a frequency range by the following expression:

$$\rho(\omega) = \rho_\infty + \frac{\rho_0 - \rho_\infty}{1 + (jf/f_c)^\alpha}$$

Fitting of the impedance model allows for identification of values for the model parameters. For the Cole-Cole impedance model, the model parameters include $\rho_0(\Omega \cdot m)$ and $\rho_\infty(\Omega \cdot m)$ the resistivities at DC and $\omega \to \infty$ respectively, f (Hz) the central frequency and the dimensionless empirical parameter $\alpha$. Evaluation of the fitting of an impedance model to calculated complex resistivity may be performed in order to determine the extent to which the model is found to fit the calculated complex resistivity. Any suitable evaluation fitting techniques may be used such as a weighted complex nonlinear least square (WCNLS) method. Additionally, initial values for the model parameters may be set as part of the fitting process.

Values for impedance model parameters may relate to certain characteristics or structural components of the muscle being assessed through multi-frequency EIM. Examples of possible histological features and related impedance model metrics are provided in the following table:

| Histological feature | Impedance-related metric |
|---|---|
| Myocyte size | Low frequency $f_c$ increased and magnitude of impedance spectrum decreased |
| Endomysial connective tissue | Low-frequency resistance values $(R_0-R_\infty)$ reduced |
| Endomysial fat | Low-frequency resistance variables elevated |
| Inflammatory cells/edema | Low-frequency reduction in anisotropic characteristics |

-continued

| Histological feature | Impedance-related metric |
|---|---|
| Mitochondrial size and health | High frequency $f_c$ and impedance spectra ($R_0$-$R_\infty$) |
| Intracellular glycogen content | Elevated high frequency $R_0$-$R_\infty$, values. |
| Vacuolization | Reduced high frequency $f_c$ |
| Intracellular organization/protein deposits | Altered anisotrophy at high frequencies |

Some embodiments include a method and apparatus for performing multi-frequency EIM measurements to identify intracellular structures of a muscle which may be used to determine a muscle condition such as a dominant muscle type for the muscle. Such approaches differentiate between muscle type based on the material properties of different muscle types. Identification of muscle type where the muscle type is unknown may include measuring one or more material properties over a range of frequencies such as approximately 1 kHz to approximately 10 MHz.

For example, skeletal muscle fibers are generally grouped into 2 broad classes of fibers: fast-twitch, commonly called type 2 fibers, and slow-twitch, commonly called type 1 fibers. Whereas there are also many subtypes of these fibers (e.g. Type Ia, Ib, IIa, etc), the broad fast- and slow-twitch distinction holds true in most appendicular muscles. Both fiber types have distinct morphology, with the slow-twitch, being mainly oxidative, contain large quantities of large mitochondria; the fast-twitch fibers, in contrast, mainly rely upon glycolytic processes, and thus have few and considerably smaller mitochondria. These differences in intracellular components between slow-twitch and fast-twitch muscles leads to different electrical properties of these two cell types.

In this example, a muscle may be identified as slow-twitch or fast-twitch muscle by analyzing the electrical signals obtained through multi-frequency EIM measurements. From the measurements, impedance parameters may be calculated, such as by fitting an impedance model as discussed above. As an example, distinguishing between slow-twitch and fast-twitch muscle may be determined by obtaining values for relative permittivity and/or conductivity.

Figure 17A:
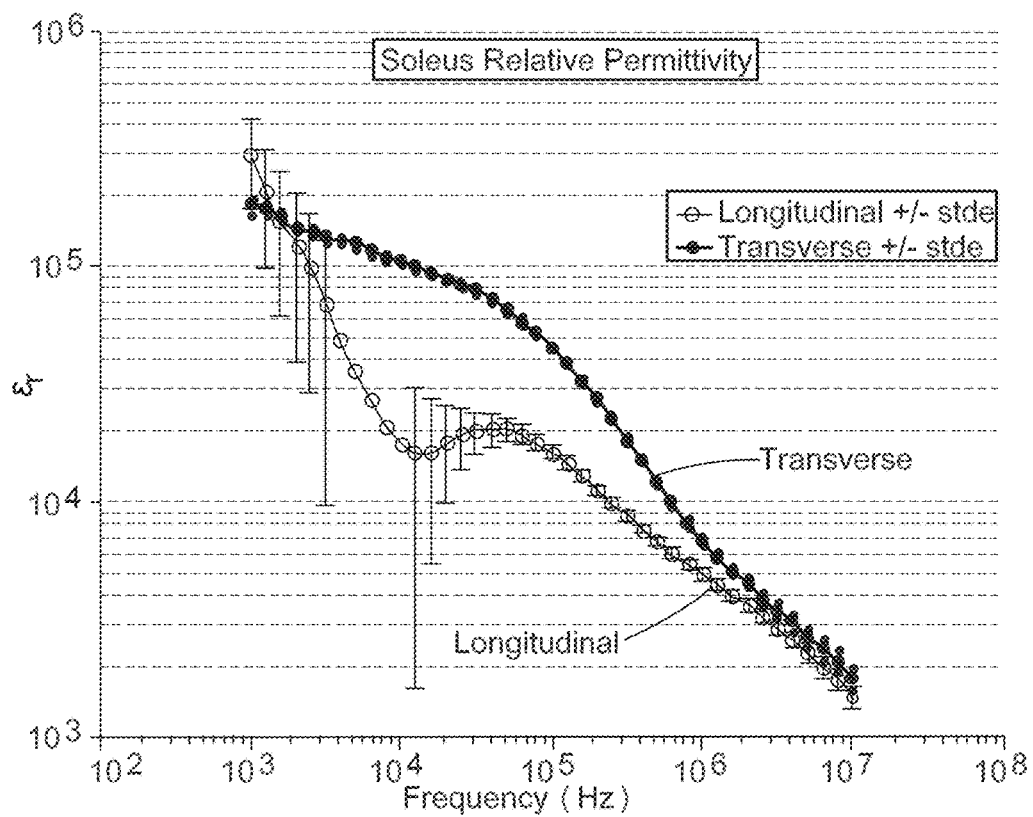
FIGS. 17A and 17B are plots of relative permittivity of the soleus and gastrocnemious muscles, respectively.
Figure 17B:
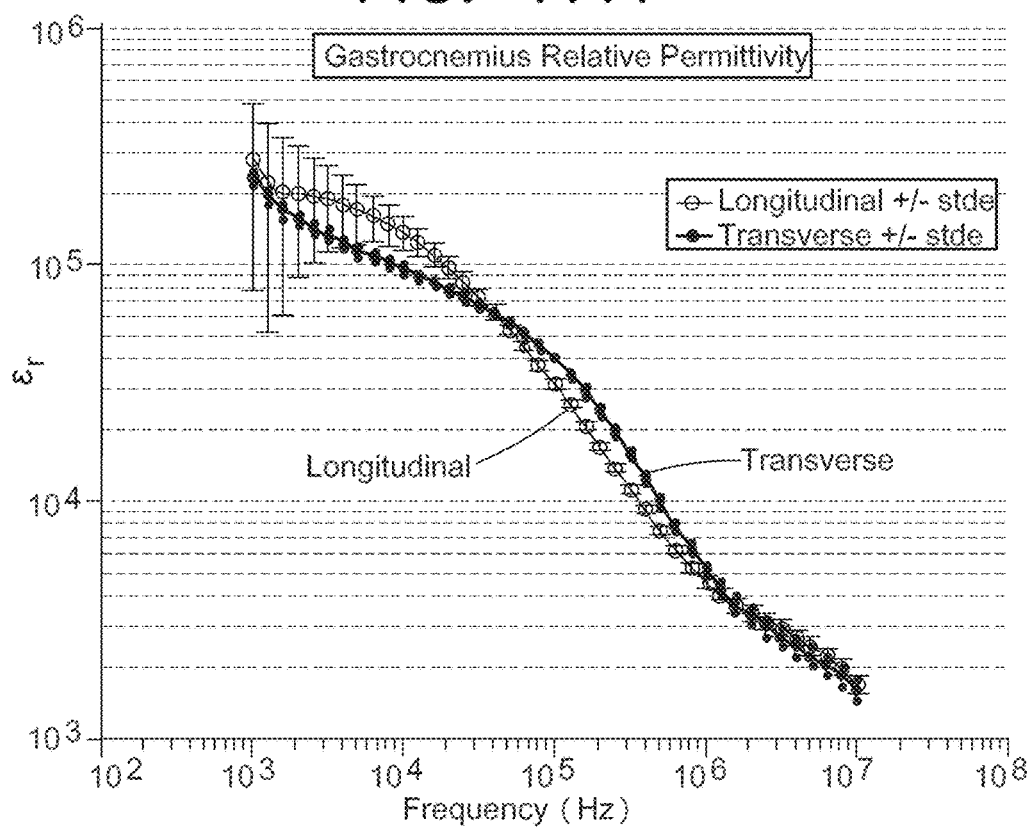
Figure 18A:
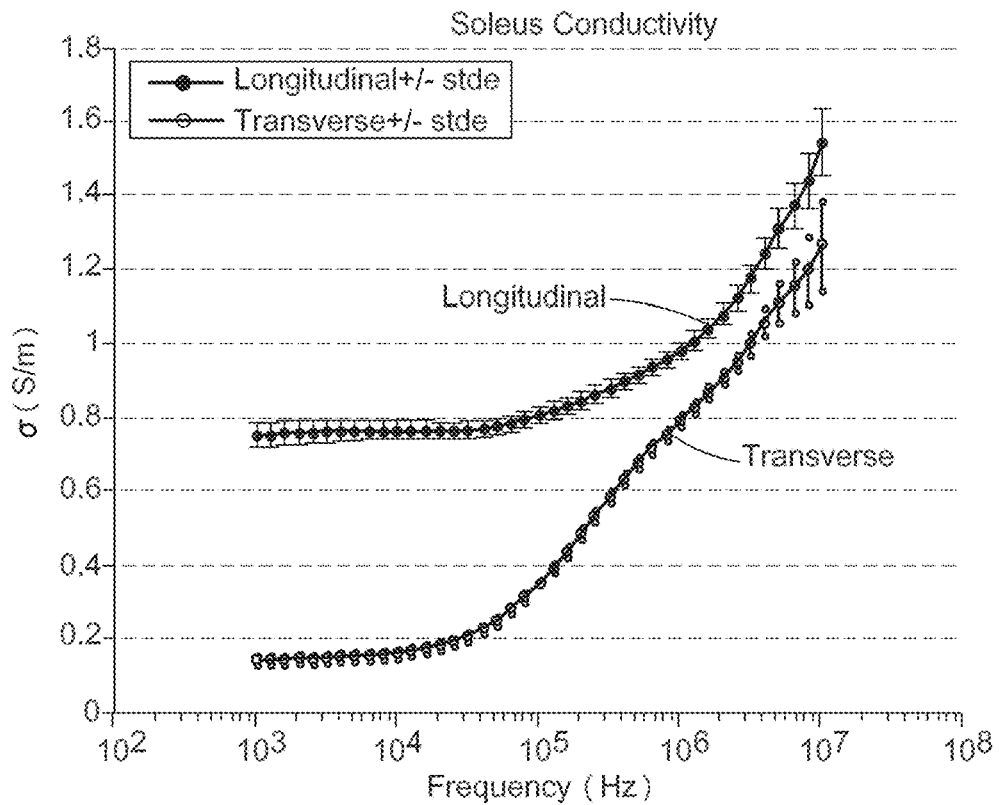
FIGS. 18A and 18B are plots of conductivity of the soleus and gastrocnemious muscles, respectively.
Figure 18B:
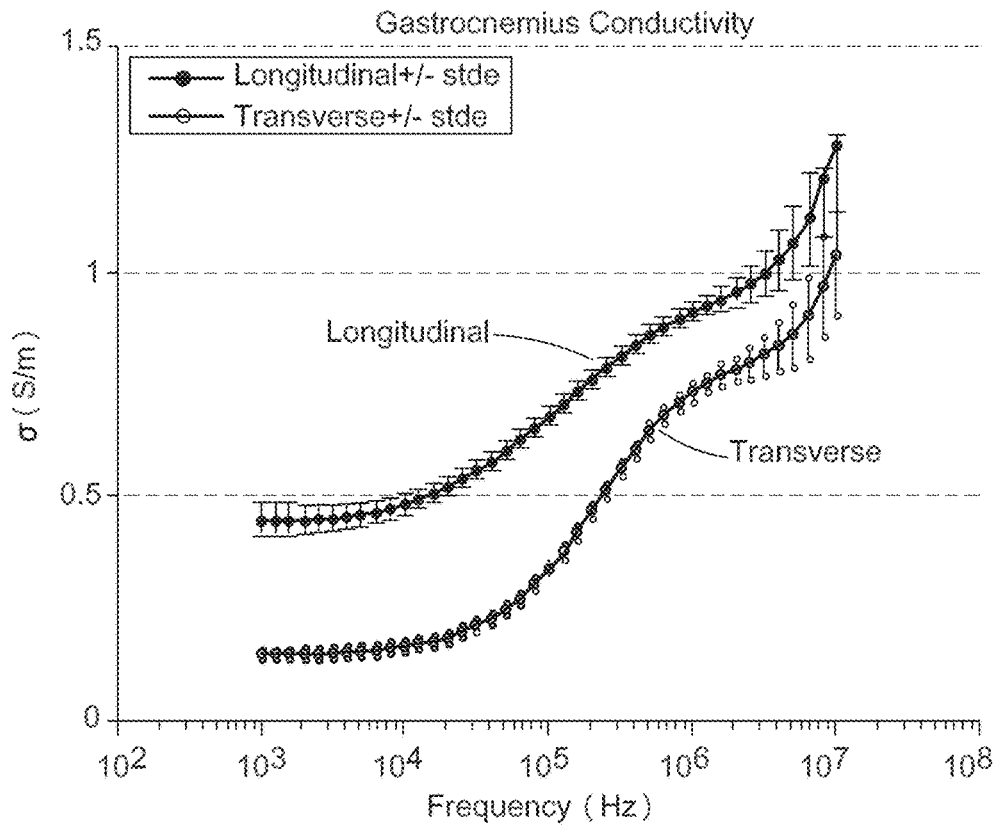
Figure 19A:
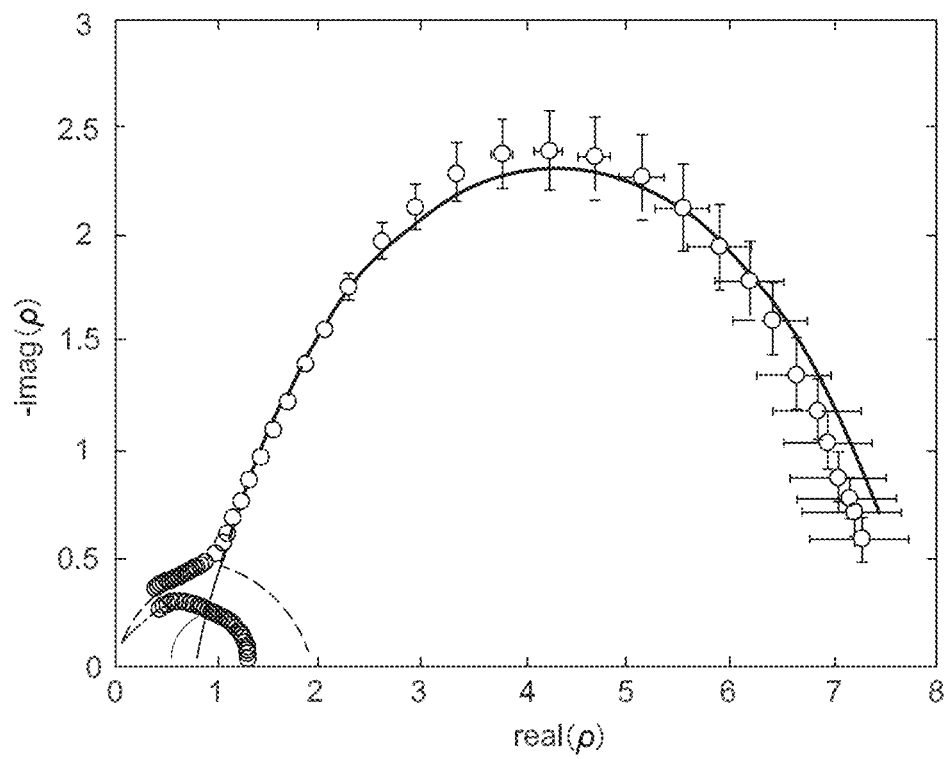
FIGS. 19A-C are plots of the complex resistivity of the soleus and gastrocnemious muscles.
Figure 19B:
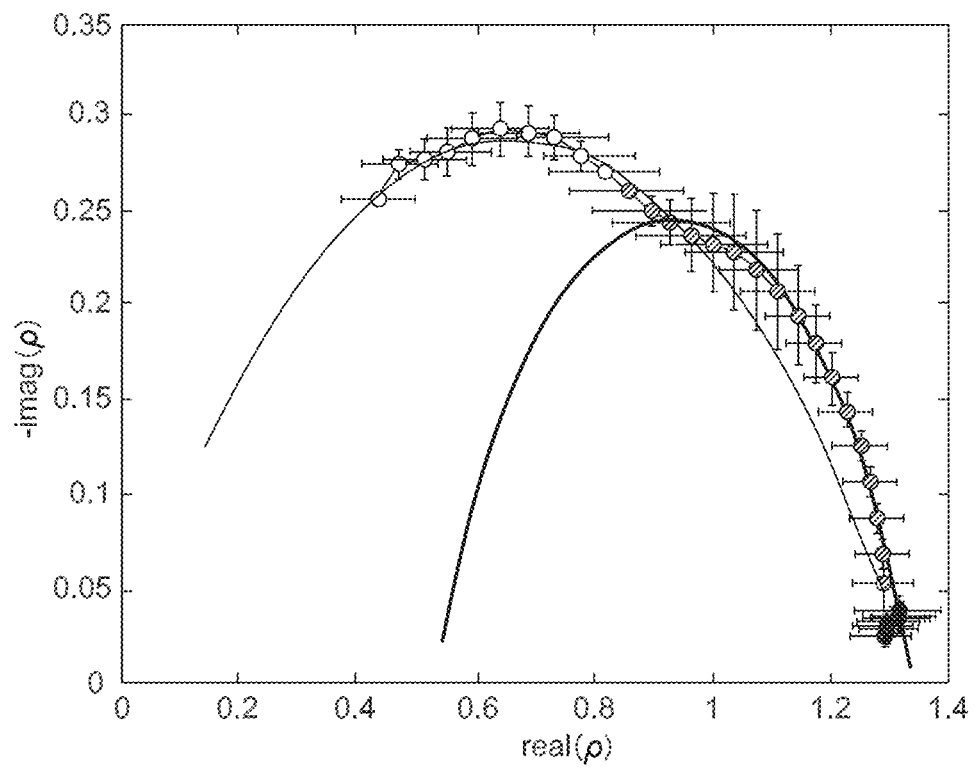
Figure 19C:
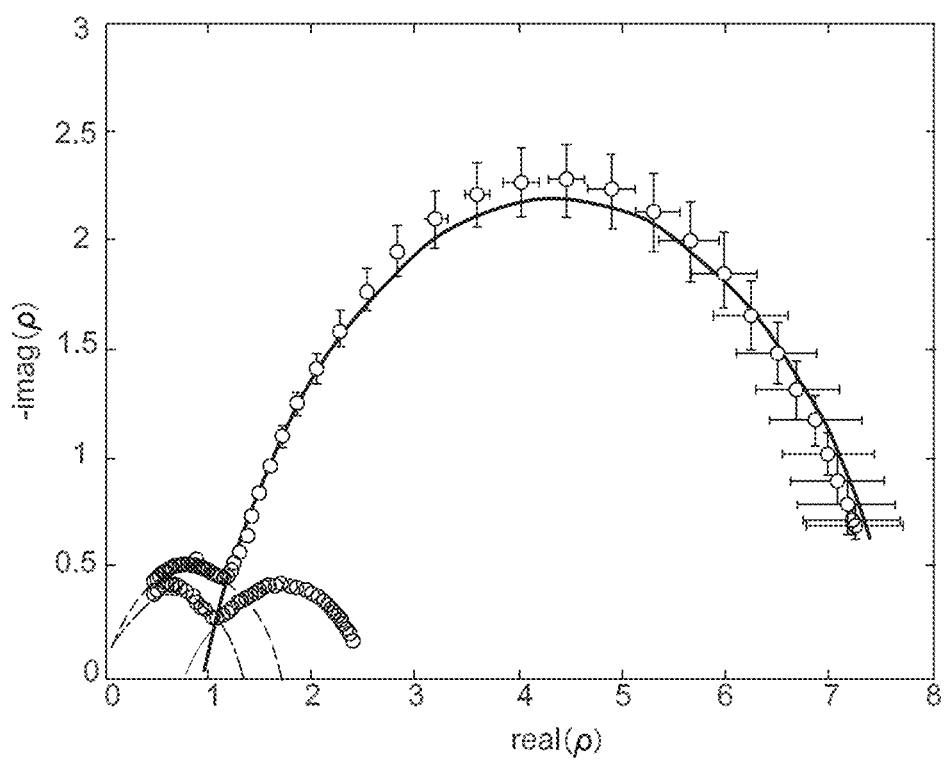

As an illustrative example, the rat soleus predominately includes slow-twitch muscle while the gastrocnemius predominately includes fast-twitch muscle. FIGS. 17A and 17B are plots of relative permittivity of the rat soleus and gastrocnemious, respectively. FIGS. 18A and 18B are plots of conductivity of the rat soleus and gastrocnemius, respectively. The relative permittivity and conductivity values over the frequency range are modeled using an impedance model such as the Cole-Cole impedance model. Results from such a modeling process include the complex resistivity as a function of frequency. FIGS. 19A and 19B are plots of the complex resistivity of soleus at different frequency ranges, and FIG. 19C is a plot of the complex resistivity of gastrocnemius. Values for impedance model parameters found by the modeling process are provided in the following tables. For example, the Cole-Cole resistivity model parameters found from data within the 1 MHz to 10 MHz frequency range for the soleus and gastrocnemius both in the longitudinal and transverse directions are as follows:

| SOLEUS | $\rho_0$ | $\rho_\infty$ | $f_c$ | $\alpha$ |
|---|---|---|---|---|
| Longitudinal | 1.3328 ± 0.0474 | 0 ± 0.0387 | 2.8796M ± 207.64k | 0.5167 ± 0.029 |
| Transverse | 1.9310 ± 0.3626 | 0 ± 0.1026 | 1.1976M ± 568.96k | 0.5605 ± 0.0953 |

| GASTROC | $\rho_0$ | $\rho_\infty$ | $f_c$ | $\alpha$ |
|---|---|---|---|---|
| Longitudinal | 1.3571 ± 0.0489 | 0 ± 0.1455 | 4.41M ± 1.036M | 0.6412 ± 0.0648 |
| Transverse | 1.7171 ± 0.0844 | 0 ± 0.0703 | 3.555M ± 306.87k | 0.6724 ± 0.0478 |

In another example, the Cole-Cole resistivity model parameters found from data within the 1 kHz to 1 MHz frequency range for the soleus and gastrocnemius both in the longitudinal and transverse directions are as follows:

| SOLEUS | $\rho_0$ | $\rho_\infty$ | $f_c$ | $\alpha$ |
|---|---|---|---|---|
| Longitudinal | 1.3389 ± 0.0075 | 0.5335 ± 0.0387 | 580.57k ± 61.682k | 0.6951 ± 0.0242 |
| Transverse | 7.8330 ± 0.1102 | 0.7929 ± 0.0242 | 18.389k ± 633.017 | 0.7365 ± 0.0090 |

| GASTROC | $\rho_0$ | $\rho_\infty$ | $f_c$ | $\alpha$ |
|---|---|---|---|---|
| Longitudinal | 2.6386 ± 0.0272 | 0.7855 ± 0.0169 | 37.837k ± 1.60k | 0.5282 ± 0.0119 |
| Transverse | 7.7636 ± 0.0882 | 0.9826 ± 0.0202 | 20.668k ± 709.045 | 0.7290 ± 0.0093 |

As discussed previously, identification and quantification of intracellular structural components, such as mitochondria, may be determined by impedance model parameters at high frequencies, such as in the high frequency arc of FIGS. 19A-C. In this case, the complete high frequency arc could be observed in the gastrocnemius data (FIG. 19C) and not in soleus data (FIG. 19A). The soleus is known to have significantly larger mitochondria such that the material properties of the mitochondria may potentially overlap with those of the cells themselves. The high frequency "tail" in the data in the lower frequency arc provides an indication of the larger size of the mitochondria. Information about the differences in the amount mitochondria between these slow-twitch and fast-twitch muscle may be observed by the $\rho_0$ and $\rho_\infty$ model values, such as the values provided in the above tables. For example, the base of the arch defined by $\rho_0$ $\rho_\infty$ may be larger for slow-twitch muscle than fast-twitch muscle, indicating a greater amount of mitochondria within slow-twitch muscle than in fast-twitch muscle. Amount of mitochondria may indicate a number, density, and/or size of the mitochondrial content within a cell. As shown with the above illustrative example, the values for the impedance model parameters may indicate information about intracellular features of the muscle being assessed through EIM where the information may be indicative of a particular condition of the muscle.

The orientation of the muscle with respect to the electrode array of the EIM probe may provide information about asymmetrical structures and components of a muscle. The example above includes multi-frequency EIM measurements performed on a muscle in both the transverse and longitudinal directions of the muscle. While differences between these two orientations of the gastrocnemius indicates the asymmetrical structure of the muscle fibers within the muscle can be illustrated in the low-frequency arc, the peak in the high-frequency arc which represents the intracellular structures such as mitochondria has only a slight anisotropy. Such information may provide further indication that the impedance model parameters are indicative of intracellular structures since features related to the orientation of the muscle fibers observed at low-frequencies can be distinguished from the intracellular components at high-frequencies.

In addition to mitochondrial content of a muscle, other types of information may be determined from the impedance model parameters such as a density of the tubule system, an amount of glycogen content, and blood supply to the muscle. In some instances, multiple aspects of the structure and content of the muscle may contribute to the observed EIM measurements and the obtained impedance model parameters through fitting. For example, a primary vascular explanation may play a role in the above results since capillaries (approximately 5 µm in diameter) are significantly smaller than muscle fibers (approximately 60 µm in diameter) and denser in slow-twitch muscle. Performing multi-frequency EIM over a range of frequencies to evaluate material properties of a muscle at high and low frequencies may allow for the assessment of muscle conditions than if EIM measurements were obtained at a single frequency or at only low frequencies.

By obtaining impedance model parameters, assessment of the conditions and/or characteristics of a muscle may be performed such as diagnosis of disease states to assess of neuromuscular conditions. For example, these techniques may assess a muscle for primary mitochondrial conditions, in which mitochondria have markedly abnormal distribution and structure. Alternatively, these techniques may evaluate other conditions with prominent intracellular abnormalities, such as lysosomal storage diseases, glycogen storage diseases, and congenital myopathies, including microtubular and nemaline rod myopathies. These techniques may also provide a measure to assess the impact of a drug on a muscle's condition such as the effectiveness of a drug to restore normal intracellular architecture including enzyme replacement therapy in Pompe's disease.

Additionally or alternatively, the techniques described herein may assess a relative proportion of fast-twitch and slow-twitch fibers in relevant muscles of an individual, providing information into the individual's physical capabilities. For example, the individual's intrinsic ability to for a particular type of activity (e.g., sprint versus run long distances) may be determined by the proportion of slow-twitch and fast-twitch muscle. Information about the proportion of slow-twitch and fast-twitch muscle may be used to assess and track the progress of an individual's exercise training program.

Some embodiments may include a method and apparatus for monitoring a muscle's condition over time through EIM measurements, also referred to as dynamic EIM. EIM measurements performed over a duration of time may provide information about changes in the condition of a muscle over the duration of time. In some embodiments, dynamic EIM may be combined with multi-frequency EIM measurements in order to obtain information from the multi-frequency EIM measurements over time. By combining dynamic EIM with multi-frequency EIM measurements, identification of impedance model parameters may be obtained at different points in time. Impedance model parameters determined from multi-frequency EIM measurements, as discussed above, may be used to assess a muscle's condition such as different stages of contraction and relaxation and evaluate contractile mechanisms of the muscle. Since some neuromuscular diseases are associated with muscle weakness, performing dynamic EIM measurements on an individual may improve assessment and diagnosis of conditions such as amyotrophic lateral sclerosis, muscular dystrophy, inflammatory myopathies, and certain polyneuropathies.

The combination of dynamic EIM with multi-frequency EIM may allow for the identification of changes of intracellular components of a muscle during stages of contract and relaxation of the muscle. In some embodiments, a reduction in a center frequency over time may be indicative of a muscle contraction. By performing EIM measurements over the duration of time where a muscle contraction occurs, the impedance data over the frequency range may be obtained. The impedance data may be modeled using an impedance model, such as a Cole-Cole impedance model, to obtain one or more Cole impedance parameters including a center frequency. Since the center frequency may correlate with the muscle diameter, as contraction occurs the muscle diameter may increase and a reduced center frequency may be observed during the muscle contraction from EIM measurements.

In some embodiments, the impedance model parameters may indicate differences between healthy versus diseased muscle. In some embodiments, the center frequency obtained during a muscle contraction may indicate that the muscle fiber size increases throughout the duration of the contraction. This relationship between center frequency and muscle fiber size may be similar for muscle associated with both healthy and diseased individuals. In some embodiments, diagnosis of a disease may be provided by identifying relationships between force intensity and one or more impedance model parameters. Since muscle strength may inversely correlate with the change in center frequency during contraction, smaller changes in force changes may be associated with greater impedance changes in diseased states as compared to healthy. In some embodiments, changes in impedance may be closely tied to development of force within a muscle and may be used to distinguish among diseased and healthy muscle. In some embodiments, changes in impedance of the muscle post-contraction as compared to pre-contraction may represent some fundamental alteration in the material properties of the muscle after contraction.

Figure 20:
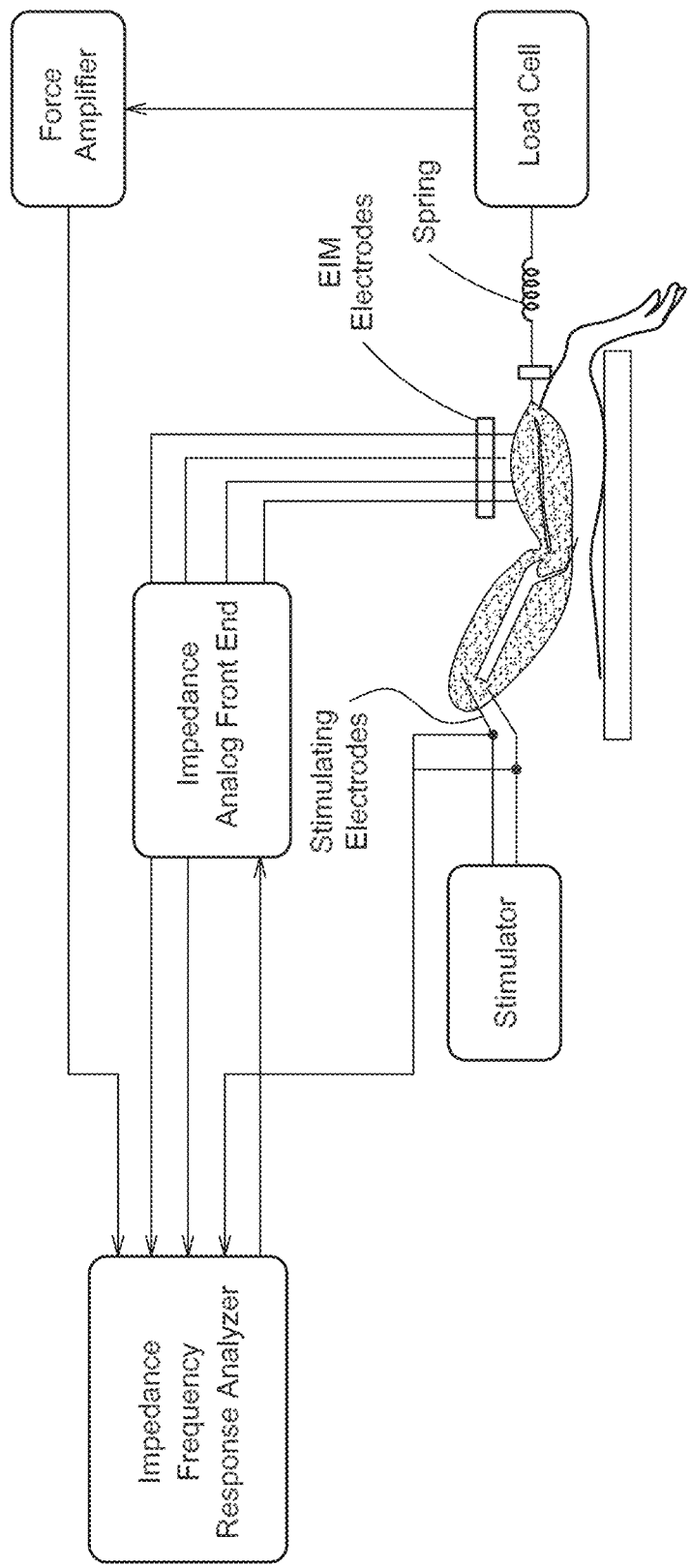
FIG. 20 is a diagram illustrating an example of a system for performing multi-frequency EIM measurements during muscle contraction.

As an illustrative example, the processes of contraction and relaxation of the gastrocnemius muscle of a rat can be identified through multi-frequency EIM measurements. Impedance model parameters can be obtained from the multi-frequency EIM measurements such as through a Cole-Cole impedance model and can be used to provide additional information about the contractile mechanisms for the gastrocnemius muscle. FIG. 20 illustrates a schematic for performing EIM measurements on a gastrocnemius muscle of a rat. The PXI-based frequency response analyzer acquires synchronously the force exerted by the gastrocnemius, the EIM and the stimuli applied to the sciatic nerve. In this example, four electrodes with an inter-electrode separation distance of 1 mm (center to center) are placed both parallel (0°) and perpendicularly (90°) to the major muscle fiber direction to assess the anisotropy determined by visual inspection. Muscle impedance measurements were obtained with a broadband impedance frequency response analyzer (FRA) implemented on a rugged PC-platform PXI (PCI eXtensions for Instrumentation). The FRA includes an embedded controller PXIe-8130, a 2 channel high-speed digitizer card PXIe-5122 (100 Ms s$^{-1}$, 64 MB/channel, 14 bits), a 9-channel digitizer card PXI-5105 (60 Ms s$^{-1}$, XX MB/channel, 12 bits) and Arbitrary Waveform Generator (AWG) card PXI-5422 (200 Ms s$^{-1}$, 32 MB, 16 bits). Synchronously to the reference excitation generated by PXI-5422, PXIe-5122 acquired both noisy current-voltage observations coming from the analog front end used to interface FRA with the electrodes. FRA analog front end consists in a drive buffers and differential amplifier; OPA656 and AD830 respectively, for high and low potential terminals and OPA656 based current-to-voltage converter for low current sensing terminal. An impedance spectrum can be computed using any suitable data processing software such as Matlab. Additionally, impedance spectrum noise may be quantified to assess the uncertainty of the impedance spectrum. The signal linear time-invariant signal processing tool used to estimate impedance may be based on the short time Fourier transform (STFT) using overlapping records. Spectral leakage was intentionally avoided by setting STFT window duration (i) by processing an integer number of periods of the reference for each record and (ii) by using a rectangular time sliding window.

For the periodic overlapped segment averaging, as this is the case, the output-input spectra were calculated using the following equation:

$$X(k) = \frac{1}{\sqrt{N}} \sum_{n=0}^{N-1} x[n] e^{-j2\pi k n T_s/N}$$

with X={V,I} the Discrete Fourier Transform (DFT) spectra, x={v,i} the noisy voltage-current observations; N the samples length of the record processed. The impedance spectrum may be estimated using the classical cross and autocorrelation spectral analysis method. The force signal and the stimuli applied to the nerve were acquired with the PXI-5105 sampling at 1 Ms s$^{-1}$.

Figure 21A:
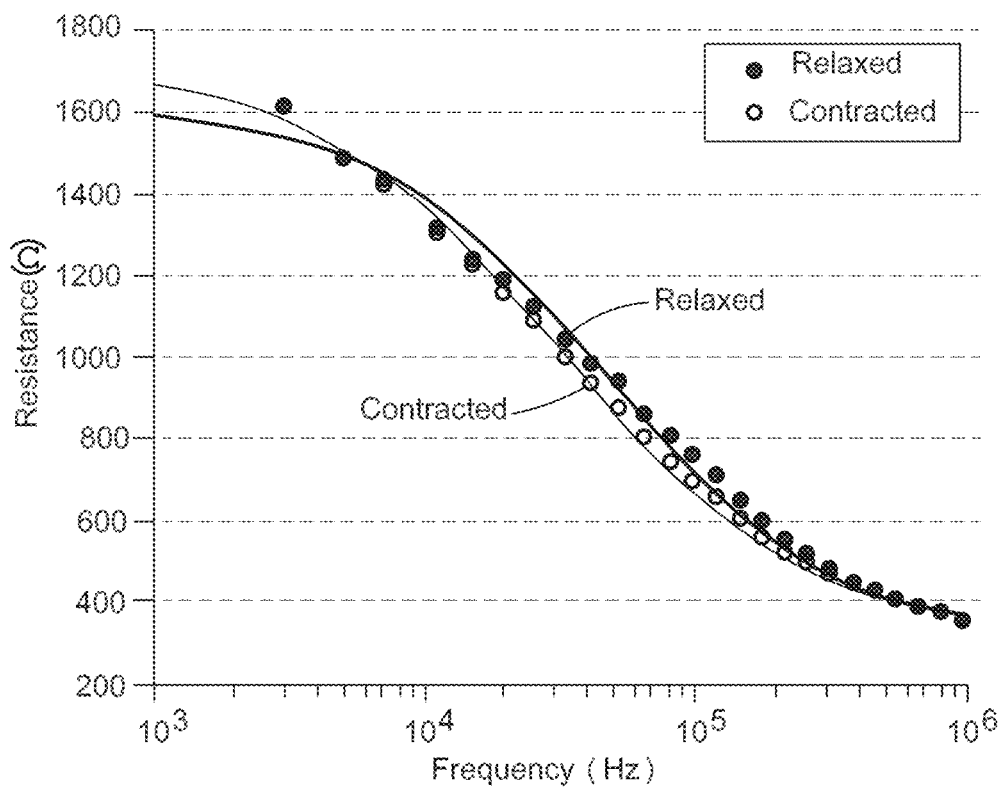
FIG. 21A-B are plots of resistance and reactance as a function of time for contracted and relaxed muscle for a wild-type animal.
Figure 21B:
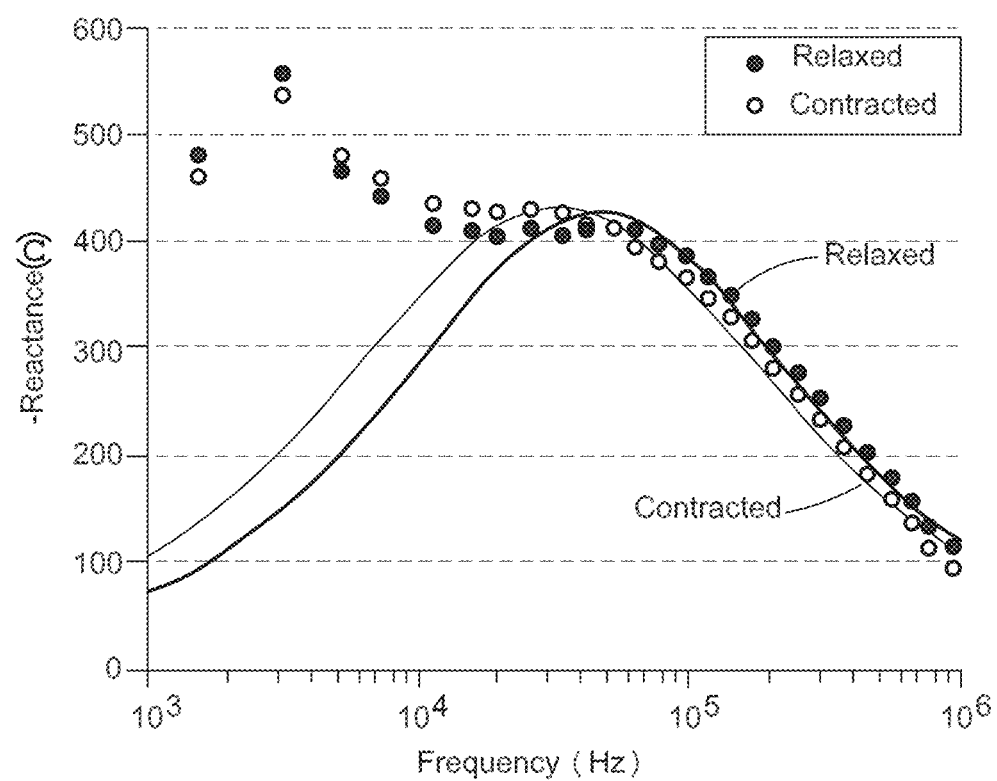

FIGS. 21A-B illustrate the resistance and reactance, respectively, for contracted and relaxed states of a gastrocnemius muscle of a wild-type animal. During contraction there is a shift in both resistance and reactance values, corresponding to an increasing amount of cellular and membrane content between the voltage-measuring electrodes. Additionally, a shift of the maximum reactance occurs when a muscle is in a contracted state.

Figure 22:
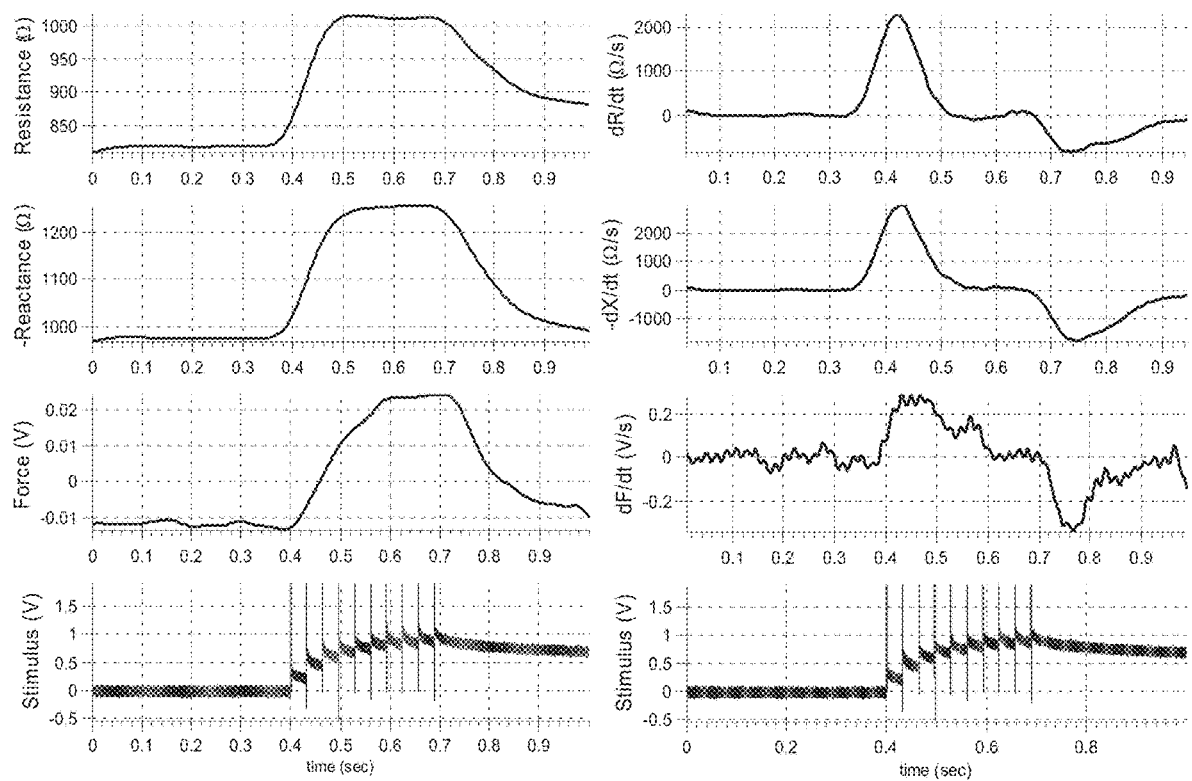
FIG. 22 are plots of resistance, reactance, and force as well as the corresponding stimuli used to produce muscle contraction as a function of time.

FIG. 22 illustrates temporal evolution of resistance, reactance, and force as well as the corresponding stimuli used to produce muscle contraction, evaluated at a frequency of 51 kHz. The right side of FIG. 22 illustrates derivative plots of that data shown on the left side of FIG. 22. From the example shown in FIG. 22, the resistance and reactance plots indicate a temporal asymmetry during a normal contract and relaxation being a slower, less-well-defined event.

Figure 23A:
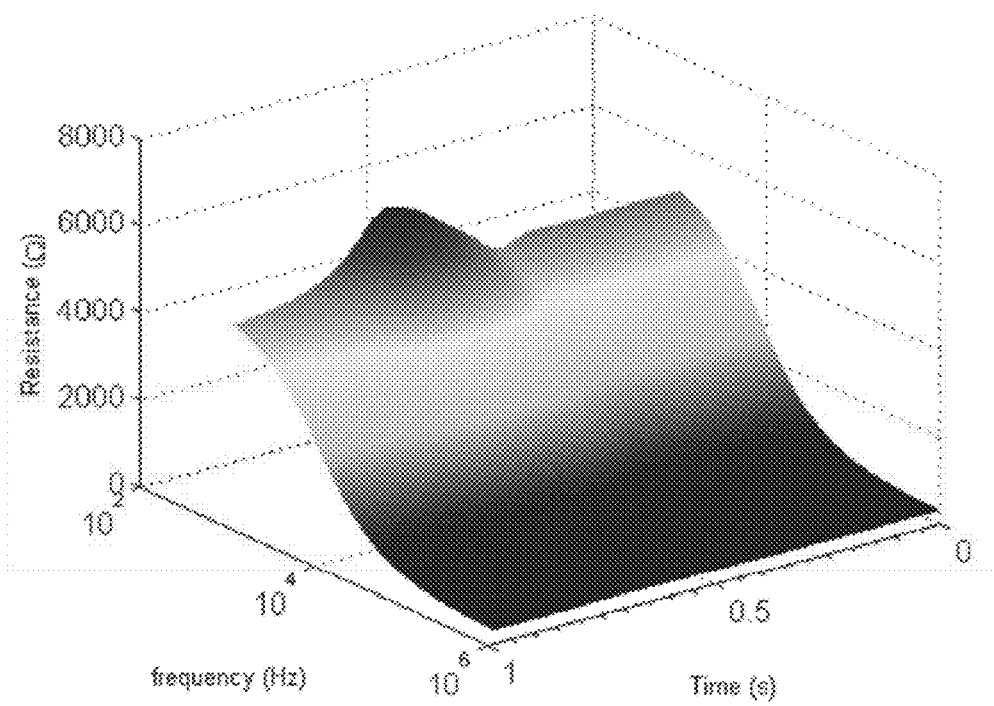
FIG. 23A-B are plots resistance and reactance as a function of frequency and time during a muscle contraction.
Figure 23B:
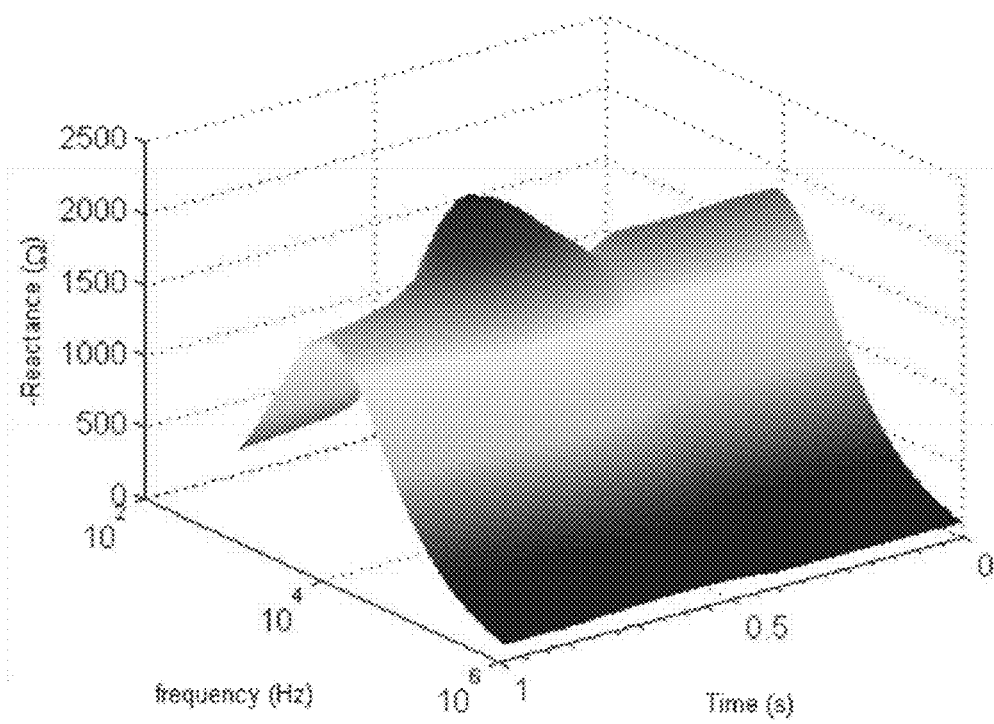

FIGS. 23A-B illustrate alternate plots of the data shown in FIGS. 21A-B and 22 and shows temporal evolution of contraction across the full range of frequencies. As shown, changes in impedance during contraction may be a small fraction of the entire muscle impedance, since muscle structure and integrity may be minimally altered during the contractile process.

Figure 24:
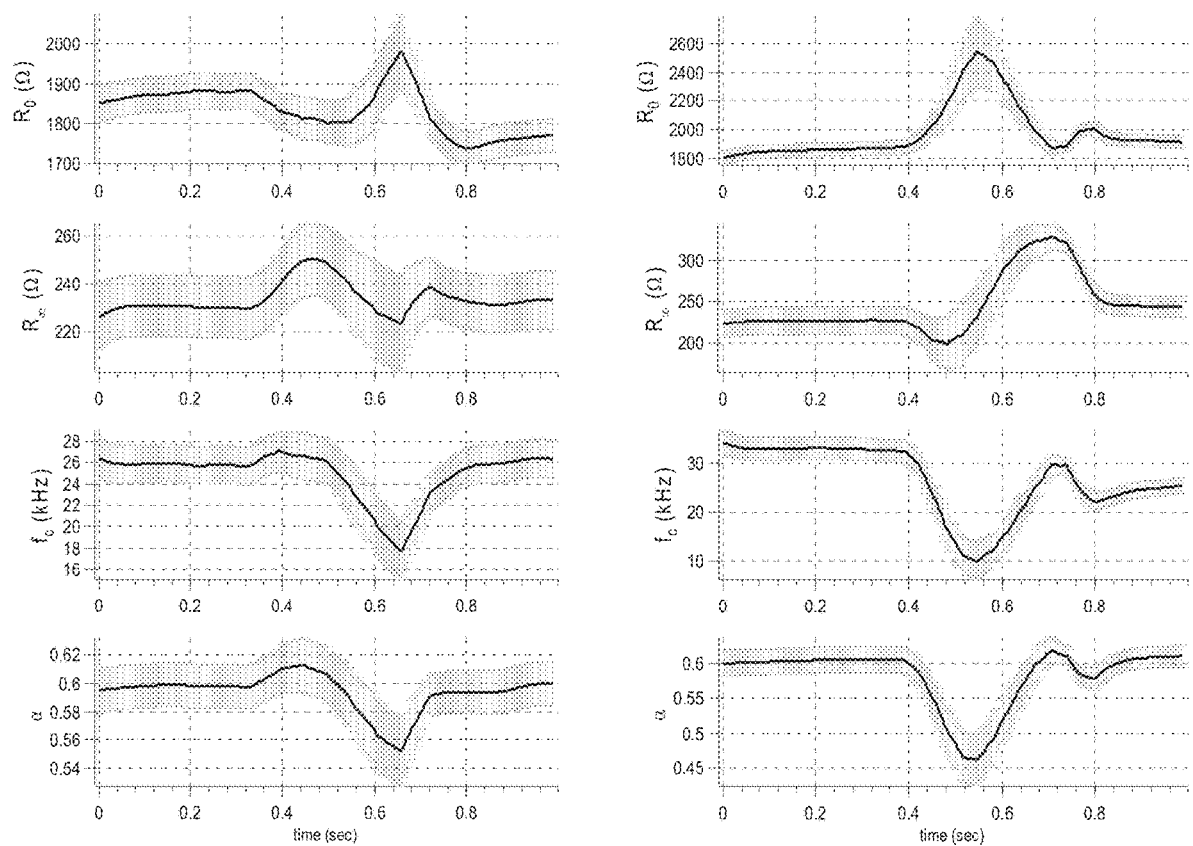
FIG. 24 are plots of Cole impedance parameters as a function of time during a muscle contraction in response to different stimuli.
Figure 25A:
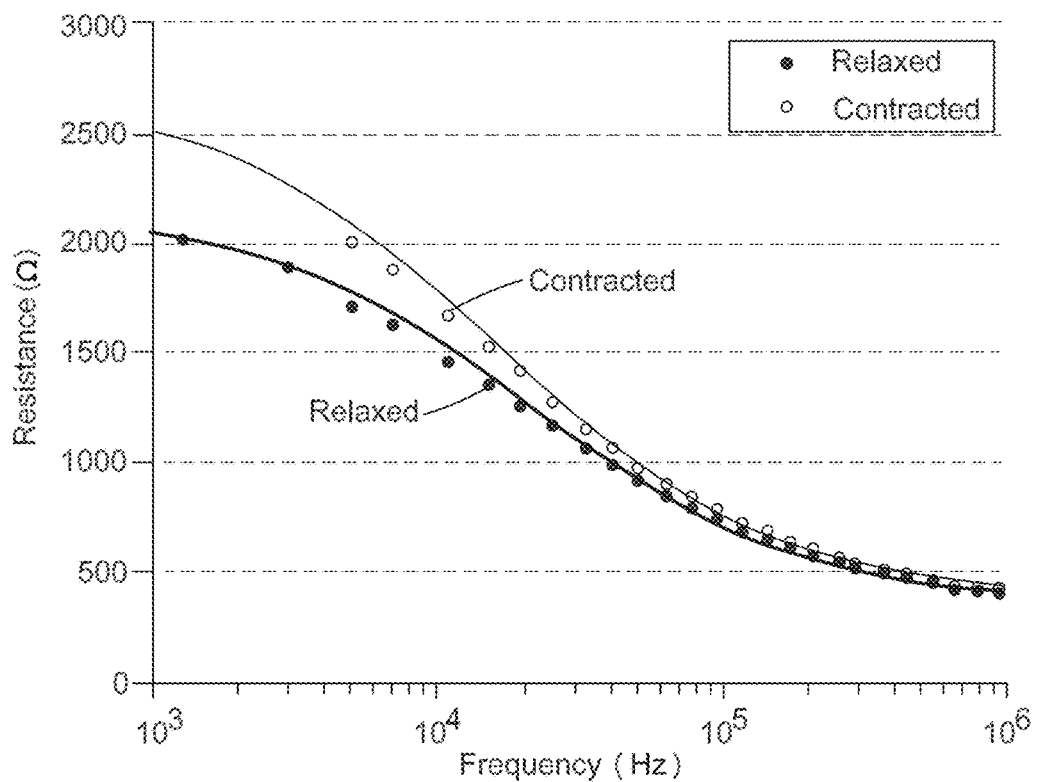
FIG. 25 are plots of are plots of resistance and reactance as a function of time for contracted and relaxed muscle for ALS (left) and Mdx (right) animals.
Figure 25B:
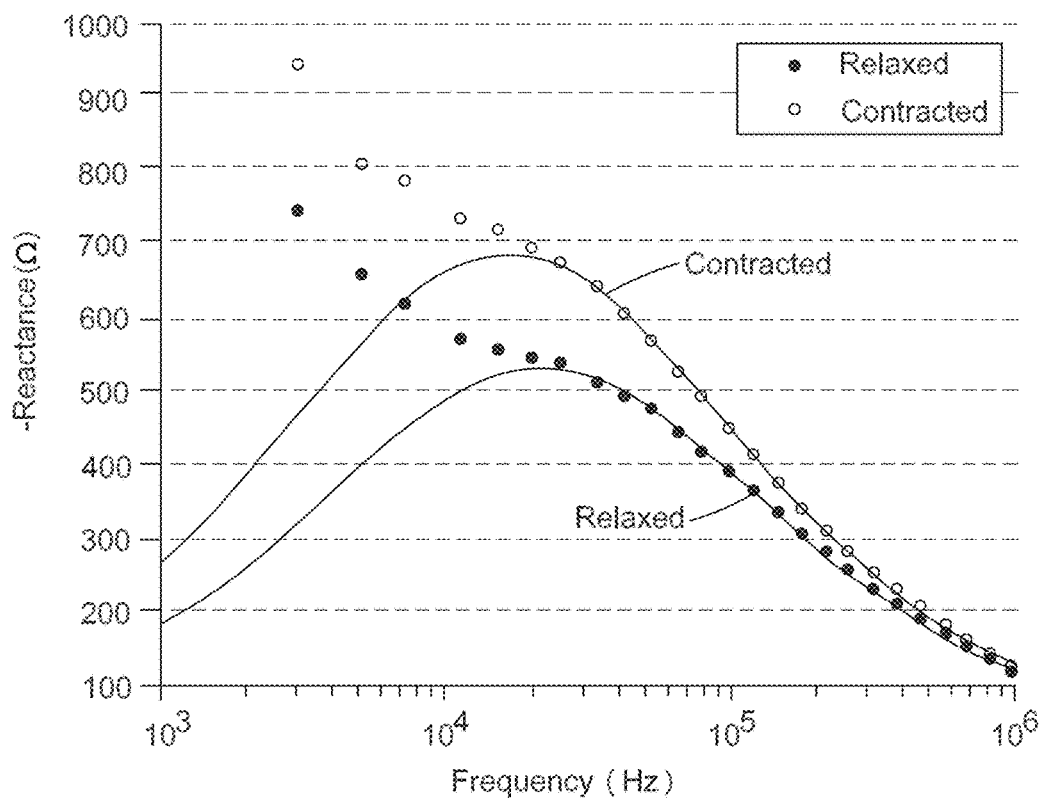
Figure 25C:
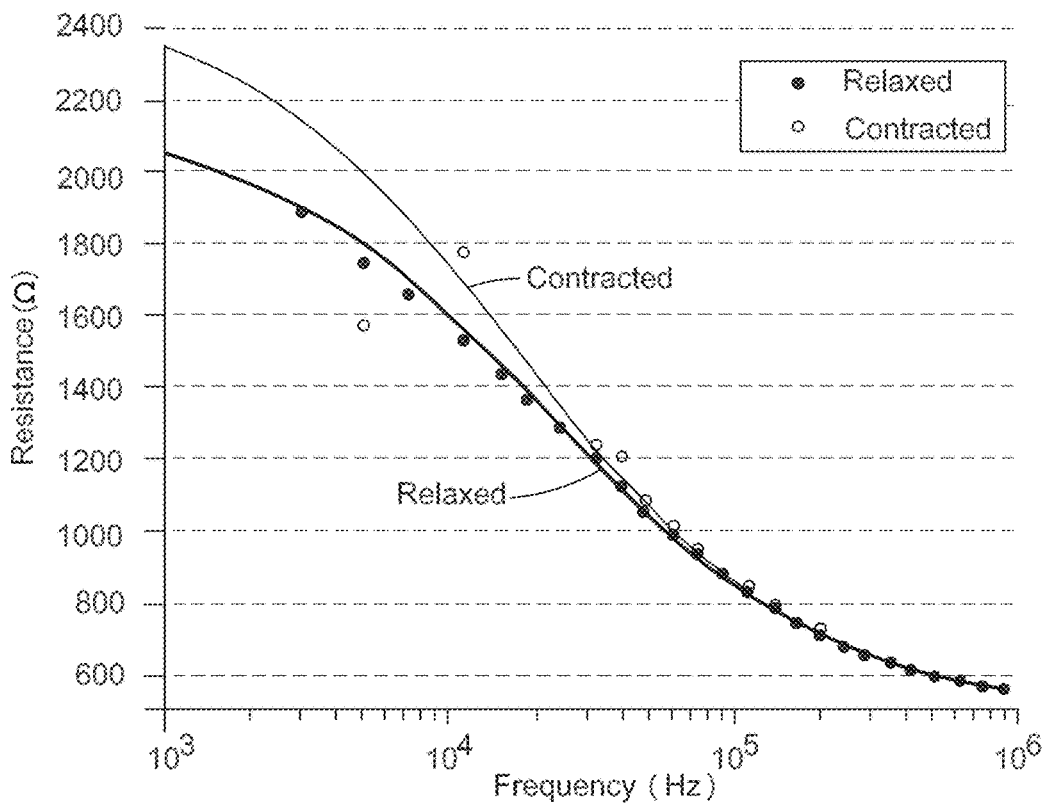
Figure 25D:
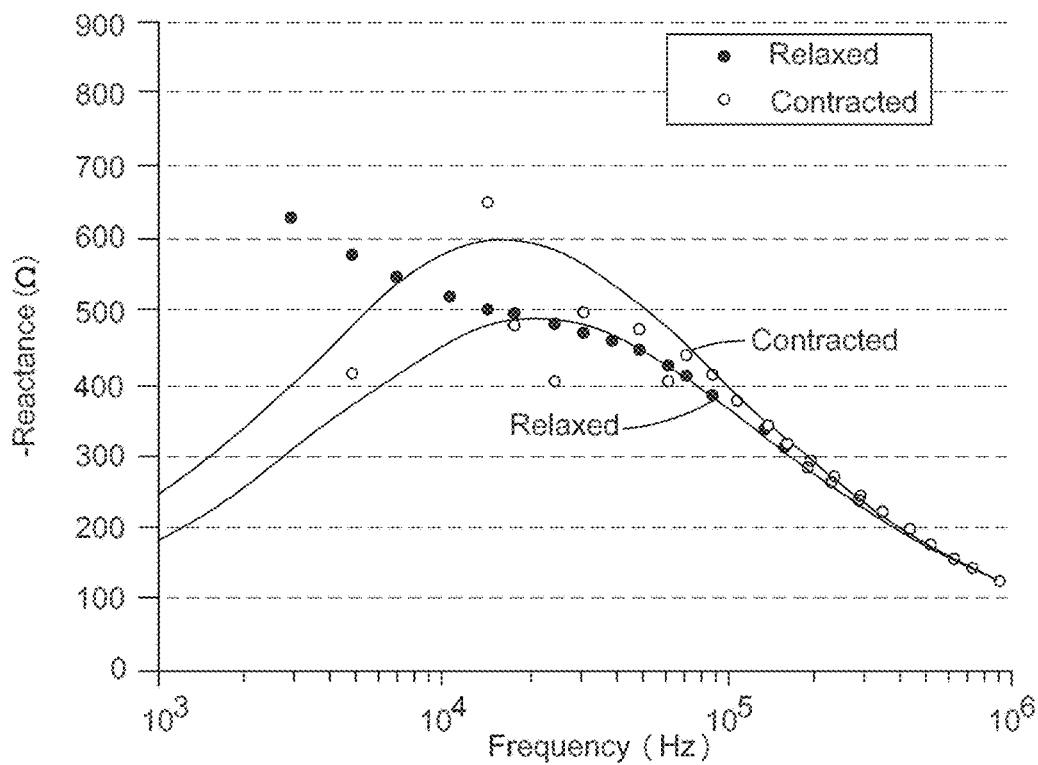

The above analysis of time-dependent multi-frequency EIM data during a contraction may be simplified through analysis of one or more Cole impedance model parameters, allowing for improved ease of interpretation of the data and assessment of the muscle. As illustrated in FIG. 24, the temporal evolution of the Cole impedance parameters—R0, R∞, fc, and alpha—for a healthy wild-type mouse. On the left side, 6 stimuli are given in that 0.33 second time period; on the right side, 10 stimuli are given in that same time period, thus producing two contractions of varying strength (the right side contraction is approximately 4 times stronger than the left).

Changes in the impedance model parameters over time may reflect changes in the muscle's condition over time. For example, impedance model parameters $R_0$ and $R_\infty$ parameters may increase during contraction and correspond to an increase in extracellular volume during contraction. As another example, the center frequency relates to the size of the muscle fiber which increases during contraction. As yet another example, alpha may correspond to uniformity of the muscle fiber size, and a reduction in alpha over the course of a muscle contraction may indicate there is a reduction in uniformity of muscle fiber size during the contraction. Additionally or alternatively, initial and final values of impedance model parameters may be analyzed to indicate differences in a muscle's condition prior to a contraction and immediately after a contraction. Such a difference in impedance model parameters initially before a contraction and after the contraction occurs may be used as an indicator of persistent alterations in the muscle's properties in the time immediately following completion of a muscle contraction.

Multi-frequency dynamic EIM measurements may be used to assess and diagnose muscle conditions associated with a weakened or diseased muscle such as a muscle affected by ALS. As an illustrative example, multi-frequency dynamic EIM measurements performed on an ALS animal and a Mdx animal in comparison to the wild-type animal discussed above may provide information about how to relate electrical parameters and/or impedance model parameters to muscle condition.

Figure 26:
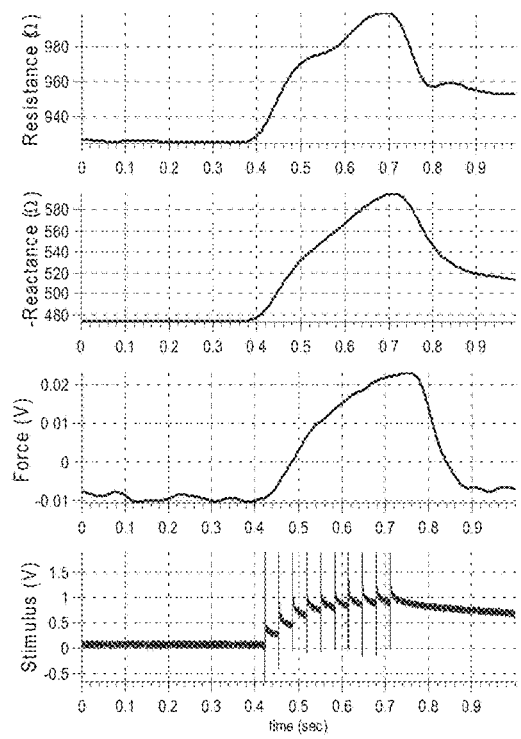
FIG. 26 are plots of resistance, reactance, and force as well as the corresponding stimuli used to produce muscle contraction as a function of time for ALS (left) and Mdx (right) animals.
Figure 26:
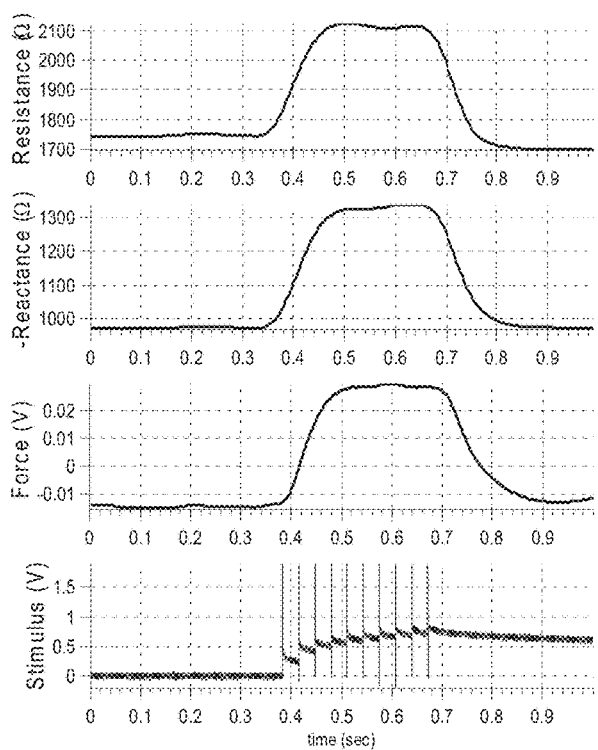

FIG. 25 shows plots for resistance and reactance spectra for an ALS animal (shown on the left) and a Mdx animal (shown on the right) with muscles in a relaxed and contracted states. The points in the plots indicate measured data while the lines represent Cole modeling data. FIG. 26 shows time dependent resistance and reactance, and the corresponding force and stimuli for ALS (shown on the left) and MDx (shown on the right) animals.

Figure 27:
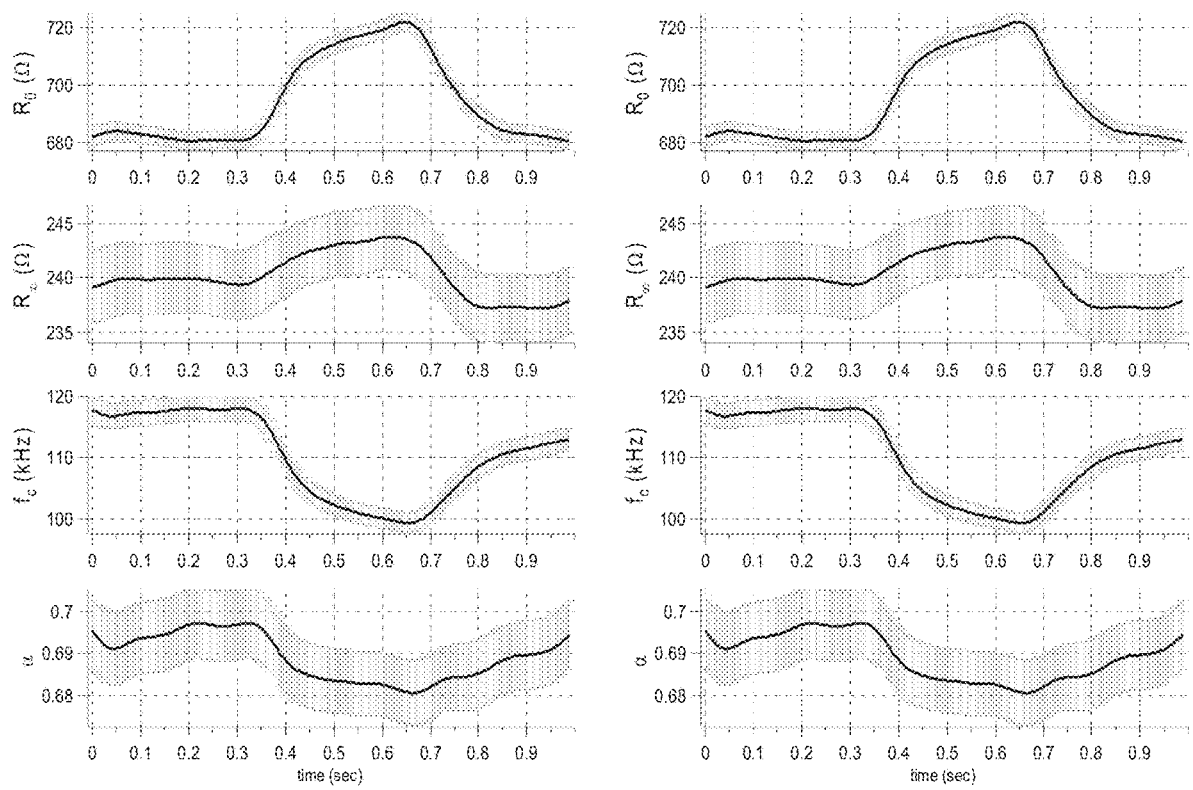
FIG. 27 are plots of Cole impedance parameters as a function of time during a muscle contraction for ALS (left) and Mdx (right) animals.

FIG. 27 illustrates Cole impedance model parameters for both the mdx and ALS animals shown in FIG. 25. The Cole impedance model parameters both between the mdx and ALS and between each of these diseased animals and the wild-type animal (shown in FIG. 21) are qualitatively different. For example, R∞, has a sudden increase in the ALS and wild-type animals, but decreases noticeably in the mdx animals. Moreover, there are substantial differences in the degree that fc changes from baseline in all 3 animal types. In the ALS animals, for example, where there is severe cell atrophy and the elevated fc shows only a relatively small change as compared to that observed in WT animals.

Figure 28:
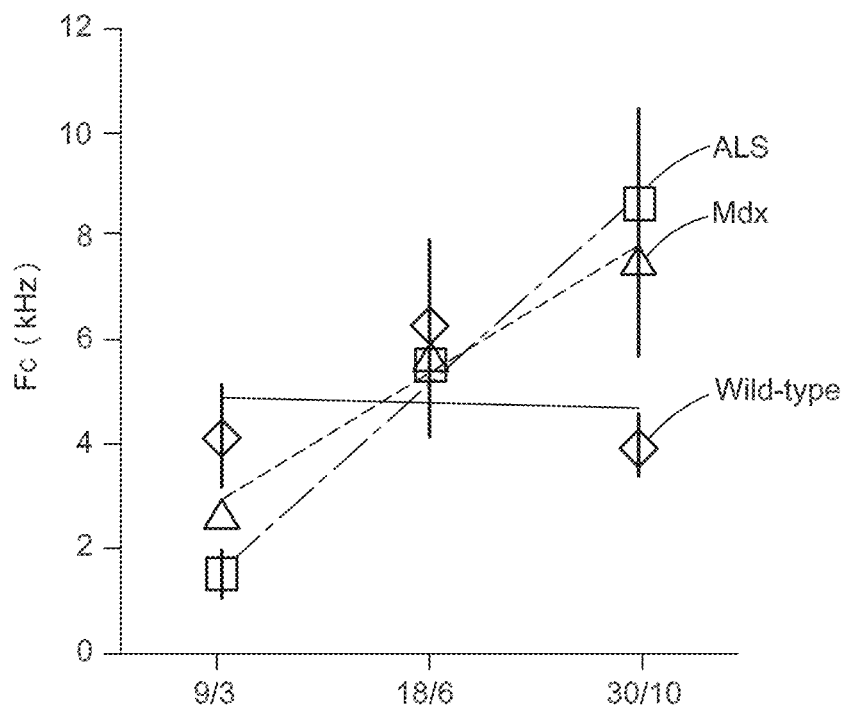
FIG. 28 is a plot of center frequency reduction during contraction as a function of stimulation rate for wild-type, ALS, and Mdx animals.

In some embodiments, one or more impedance model parameters may relate to muscle contraction and the neuronal input for the muscle contraction. As an illustrative example, FIG. 28 shows the relationship between stimulation rate (ie strength of induced contraction) and the center frequency reduction for wild-type, ALS, and Mdx animals. WT animals demonstrate a near constant change in center frequency across the stimulation rates, whereas the mdx and ALS animals both show a much more dramatic relationship, with the reduction in center frequency being greater with stronger contractions. Such data may reveal important information on the overall ability of a muscle contract and the neuronal input needed to produce a sufficiently powerful contraction.

Figure 29:
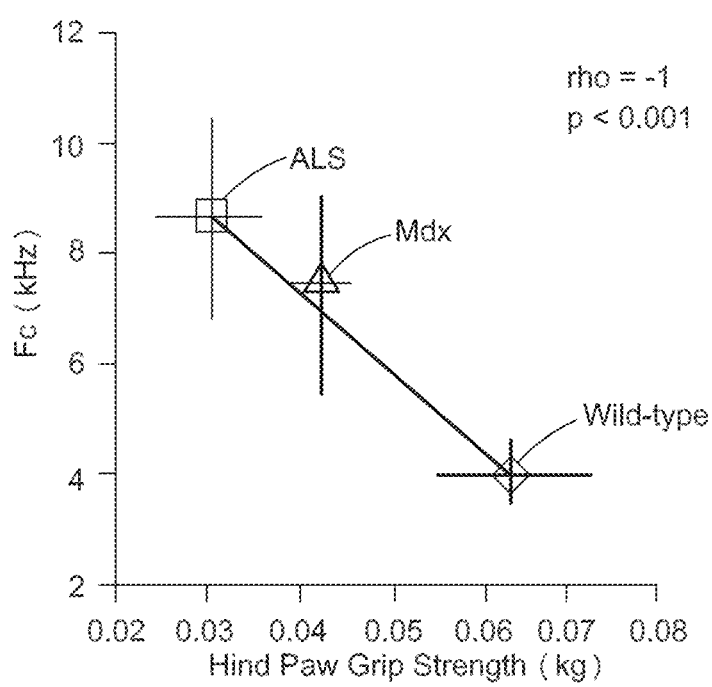
FIG. 29 is a plot of center frequency reduction during contraction as a function of hind limb strength wild-type, ALS, and Mdx animals.

In some embodiments, one or more impedance model parameters may correspond to strength of the muscle. As an illustrative example, FIG. 29 shows the relationship between hind limb strength (measured during voluntary contraction) and the change in center frequency with contraction. As can be seen, the weaker animals demonstrate greater changes in center frequency than healthier ones, all stimulation parameters being kept the same (30 Hz stimuli).

Figure 30:
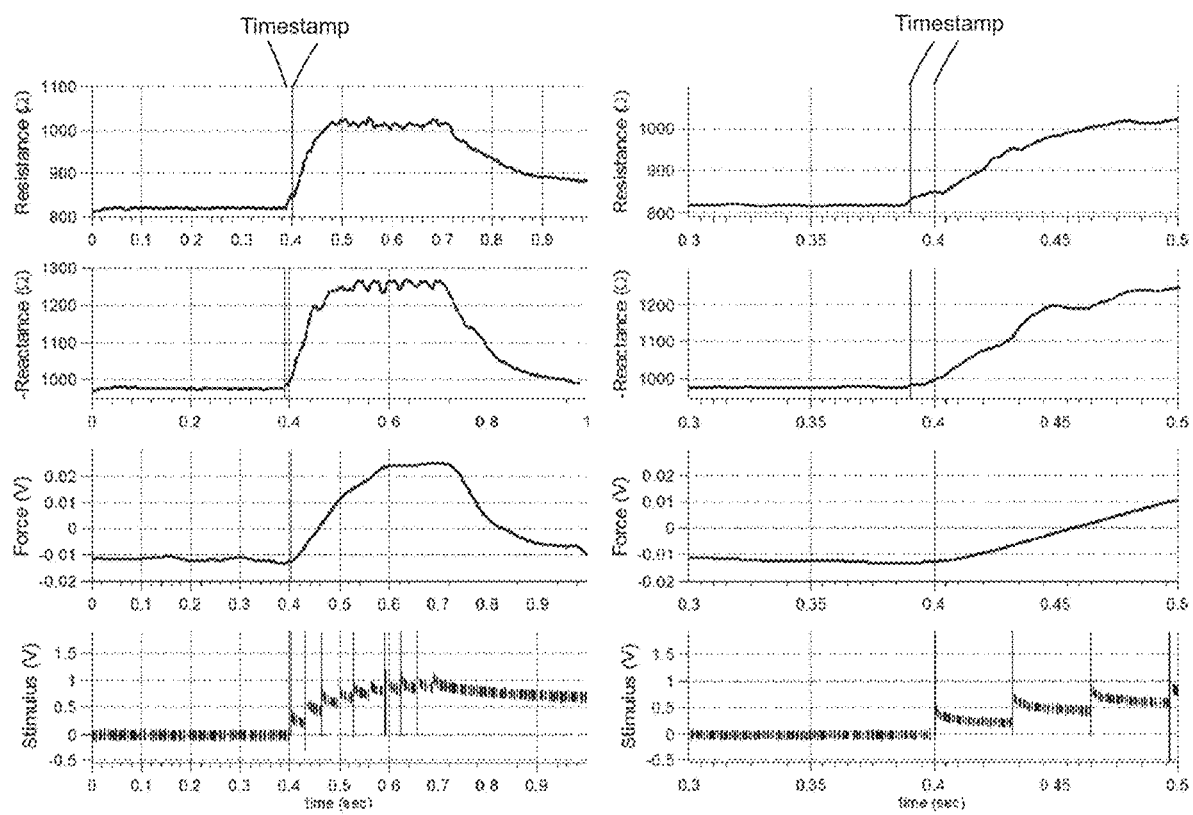
FIG. 30 are plots of resistance, reactance, and force as well as the corresponding stimuli used to produce muscle contraction as a function of time with time stamps.

Some embodiments relate to methods and apparatus for synching EIM measurement techniques with dynamic measurement of muscle contraction. FIG. 30 provides an illustrative example were a time stamp shows where the first stimulus occurred, and an additional time stamp is provided in the impedance plots to mark the temporal duration of a short time Fourier transform (STFT) window. Thereafter, any onset change in impedance in between the two time stamps, however small and a part from the noise, is because of the overlapping process performed on the data processed with the STFT. Thus, the onset of the impedance change does not precede the onset of the force.

Any of the techniques described above may be used to track a condition of a muscle over a period of time (e.g., days, weeks, months, years). EIM measurements may be performed at time points throughout the period of time to monitor changes in a muscle's condition. In some embodiments, temporal data related to the EIM measurements may be collected and analyzed as part of the assessment process, and in some embodiments may be compared to previously acquired data such as data acquired from the same muscle, other muscles, and/or other individuals. For example, one or more impedance model parameters obtained by EIM measurements performed on a muscle may be used to monitor the condition of the muscle over time.

Some embodiments relate to methods and apparatus for performing EIM measurements over a duration of time to monitor the effects of exercise on an individual's muscle condition. EIM measurements may be made before, during, and/or after an exercise session to assess changes in a muscle's condition due to the exercise session. In some embodiments, EIM measurements may be performed on one or more on an individual's muscles prior to an exercise session and shortly after the exercise session to assess acute changes to the condition of the muscle. Additionally or alternatively, long term changes to muscle condition due to exercise may be assessed and monitored by periodically performing EIM measurements on one or more muscles. One or more impedance model parameters may be used to identify any changes in the muscle's condition from the individual's participation in multiple exercise sessions or an exercise program. The one or more impedance model parameters may indicate a change in the characteristic of the muscle including muscle type (e.g., slow-twitch, fast-twitch), strength, muscle fiber size, or any suitable characteristic has discussed above. By identifying how certain characteristics of an individual's muscle changes over time due to exercise, the effectiveness of the exercise sessions and/or program may be assessed and evaluated. In this manner, an individual may obtain physiological feedback about how exercise can impact one or more muscles of the individual.

The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method comprising:
applying, using a plurality of electrodes, a plurality of electrical signals having a plurality of frequencies to a region of tissue, wherein an electrical signal of the plurality of electrical signals has one frequency of the plurality of frequencies;
obtaining a plurality of measurements from the region of tissue in response to applying the plurality of electrical signals, wherein each measurement of the plurality of measurements is indicative of an electrical parameter of the region of tissue at one frequency of the plurality of frequencies;
determining, using computer circuitry, one or more values for at least one impedance model parameter associated with an impedance model, at least in part, by fitting a plurality of values of the electrical parameter for the plurality of frequencies to the impedance model, wherein the at least one impedance model parameter includes a frequency and determining the one or more values for at least one impedance model parameter further comprises determining a value for the frequency; and determining muscle fiber type in the region of tissue by using the value for the frequency to identify at least one biological characteristic of the region of tissue.

2. The method of claim 1, wherein the muscle fiber type is at least one of fast-twitch and slow-twitch.

3. The method of claim 1, wherein the at least one biological characteristic includes an amount of an intracellular component.

4. The method of claim 1, wherein the at least one biological characteristic includes a structural feature of an intracellular component.

5. The method of claim 4, wherein the intracellular component is mitochondrion.

6. The method of claim 1, further comprising, assessing a muscle condition based on the muscle fiber type.

7. The method of claim 1, further comprising, diagnosing a disease state based on the muscle fiber type.

8. The method of claim 1, wherein the impedance model is a Cole-Cole complex resistivity model and the at least one impedance model parameter is at least one of resistance at direct current (DC), $R_0$, resistance as $\omega \to \infty$, $R_\infty$, central frequency, $f_c$, and dimensionless parameter, $\alpha$.

9. The method of claim 8, wherein resistance at direct current and resistance as $\omega \to \infty$ indicate a characteristic of the volume of the cells in the biological tissue.

10. The method of claim 9, wherein dimensionless parameter, $\alpha$, indicates a degree of uniformity of fiber size when the biological material includes muscle fibers.

11. The method of claim 8, wherein the central frequency indicates a diameter of muscle fiber when the biological tissue includes a muscle fiber.

12. The method of claim 8, wherein the central frequency is monitored before, during, and after a muscle contraction and indicates a condition of a muscle located at the region of tissue.

13. The method of claim 1, wherein the at least one impedance model parameter is monitored before and after a muscle contraction and determines a change of the region of tissue from the contraction.

14. The method of claim 1, wherein the frequency is a reactance frequency.

15. The method of claim 14, wherein determining muscle fiber type in the region of tissue is based on the reactance frequency.

16. The method of claim 1, wherein applying the plurality of electrical signals to the region of tissue and obtaining the plurality of measurements from the region of tissue are both performed while muscle in the region of tissue is in a relaxed state.

17. The method of claim 1, wherein applying the plurality of electrical signals to the region of tissue further comprises applying the plurality of electrical signals at different orientations with respect to the muscle fibers in the region of tissue.

18. The method of claim 6, wherein assessing the muscle condition further comprises diagnosing the muscle condition as being at least one selected from the group consisting of amyotrophic lateral sclerosis, muscular dystrophy, disuse atrophy, and congenital myopathy.

* * * * *